US006403588B1

(12) United States Patent
Hayakawa et al.

(10) Patent No.: US 6,403,588 B1
(45) Date of Patent: Jun. 11, 2002

(54) IMIDAZOPYRIDINE DERIVATIVES

(75) Inventors: Masahiko Hayakawa; Hiroyuki Kaizawa; Ken-Ichi Kawaguchi; Koyo Matsuda; Noriko Ishikawa; Tomonobu Koizumi; Mayumi Yamano; Minoru Okada; Mitsuaki Ohta, all of Tsukuba (JP)

(73) Assignees: Yamanouchi Pharmaceutical Co., Ltd., Tokyo (JP); Ludwig Institute for Cancer Research, New York, NY (US); Imperial Cancer Research Technology, Ltd., London (GB)

( * ) Notice: Subject to any disclaimer, the term of this patent is extended or adjusted under 35 U.S.C. 154(b) by 0 days.

(21) Appl. No.: 09/843,610

(22) Filed: Apr. 26, 2001

Related U.S. Application Data

(60) Provisional application No. 60/200,173, filed on Apr. 27, 2000.

(51) Int. Cl.$^7$ .................... A61K 31/435; C07D 471/04
(52) U.S. Cl. ................. 514/249; 514/300; 514/303; 544/236; 546/119; 546/120; 546/121
(58) Field of Search ................. 546/121, 119, 546/120; 544/236; 514/300, 303, 249

(56) References Cited

U.S. PATENT DOCUMENTS 4,735,956 A    4/1988    Baldwin et al. ............ 514/338

FOREIGN PATENT DOCUMENTS

| EP | 430385 | 6/1991 |
|---|---|---|
| JP | 377881 | 4/1991 |
| WO | 0181346 | 11/2001 |

OTHER PUBLICATIONS

The Rearrangement of 2–Nitroenamines in Acidic Solutions, Krowczynski, et al.—Bull. Pol. Acad. Sci., Chem. 1986, 34 (7–8), p. 341–349.

Synthesis of Pyridylthiazoles as antisecretory agents, Kosary, et al., Pharmazie, 44(3), 1989, p. 1919–193.

Synthesis of Some 4–Thiazoline and 4H–1,2,4–riazole . . . Possible Anticonvulsants, Cesur, et al. Farmaco, 49(10), 1994, p. 679–681.

*Primary Examiner*—Bernard Dentz
(74) *Attorney, Agent, or Firm*—Fulbright & Jaworski, L.L.P.

(57) ABSTRACT

The present invention relates to novel compounds having a phosphatidylinositol 3 kinase (PI3K) inhibiting activity which are useful as medicaments, more particularly as antitumor agent. Novel 3-(imidazo[1,2-a]pyridin-3-yl) derivatives or salts thereof exhibit an excellent PI3K inhibiting activity and cancer cell growth inhibiting activity, and are thus useful as medicaments, especially as PI3K inhibitors and antitumor agents.

12 Claims, No Drawings

IMIDAZOPYRIDINE DERIVATIVES

This application claims benefit of Provisional Application Ser. No. 60/200,173 filed Apr. 27, 2000.

FIELD OF THE INVENTION

The present invention relates to imidazolidine derivatives which are useful as medicaments, more particularly as phosphatidylinositol-3-kinase (PI3K) inhibitors and antitumor agents.

BACKGROUND OF THE INVENTION

Phosphatidylinositol (hereinafter abbreviated as "PI") is one of a number of phospholipids found in cell membranes. In recent years it has become clear that PI plays an important role in intracellular signal transduction. It is well recognized in the art that especially PI (4,5) bisphosphate (PI(4,5)P2) is degraded into diacylglycerol and inositol (1,4,5) triphosphate by phospholipase C to induce activation of protein kinase C and intracellular calcium mobilization, respectively [M. J. Berridge et al., Nature, 312, 315 (1984); Y Nishizuka, Science, 225, 1365 (1984)].

Turning back to the late 1980s, a PI3 kinase (PI3K) was found to be an enzyme to phosphorylate the 3-position of the inositol ring of phosphatidylinositol [D. Whitrnan et al., Nature, 332, 664 (1988)].

PI3K was originally considered to be a single enzyme at the time when PI3K was discovered. Recently it was clarified that a plurality of subtypes are present in the PI3K. Three major classes of PI3Ks have now been identified on the basis of their in vitro substrate specificity [B. Vanhaesebroeck, Trend in Biol. Sci., 22, 267(1997)].

Substrates for class I PI3Ks are PI, PI(4)P and PI(4,5)P2. In these substrates, PI(4,5)P2 is the most advantageous substrate in cells. Class I PI3Ks are further divided into two groups, class Ia and class Ib, in terms of their activation mechanism. Class Ia PI3Ks, which include PI3K p110α, p110β and p110δ subtypes, are activated in the tyrosine kinase system. Class Ib PI3K includes a p110γ subtype activated by a G protein-coupled receptor.

PI and PI(4)P are known as substrates for class II PI3Ks but PI(4,5)P2 is not a substrate for the enzymes of this class. Class II PI3Ks include PI3K C2α, C2β and C2γ subtypes, which are characterized by containing C2 domains at the C terminus, implying that their activity will be regulated by calcium ions. The substrate for class III PI3Ks is PI only. A mechanism for activation of the class III PI3Ks is not clarified yet. Since each subtype has its own mechanism for regulating activity, it is considered that the respective subtypes will be activated depending on their respective stimuli specific to each of them.

In the PI3K subtypes, the class Ia subtype has been most extensively investigated to date. The three subtypes of class Ia are hetero dimers of a catalytic 110 kDa subunit and regulatory subunits of 85 kDa and 55 kDa. The regulatory subunits contain SH2 domains and bind to tyrosine residues phosphorylated by growth factor receptors with a tyrosine kinase activity or oncogene products thereby inducing the PI3K activity of the p110 catalytic subunit. Thus, the class Ia subtypes are considered to be associated with cell proliferation and carcinogenesis. Furthermore, the class Ia PI3K subtypes bind to activated ras oncogene to express their enzyme activity. It has been confirmed that the activated ras oncogene is found to be present in many cancers, suggesting a role of class Ia PI3Ks in carcinogenesis.

As explained above, the PI3K inhibitors are expected to be a new type of medicaments useful for cell proliferation disorders, in particular antitumor agents. As the PI3K inhibitor, wortnannin[H. Yano et al., J. Biol. Chem., 263, 16178 (1993)] and Y294002 [J. Vlahos et al., J. Biol. Chem., 269, 5241(1994)] which is represented by the formula below are known. However, creation of PI3K inhibitors are sincerely desired having a more potent and excellent cancer cell growth inhibiting activity.

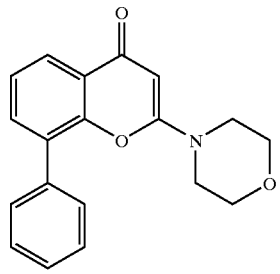

LY294002

Japanese patent KOKAI (Laid-Open) No. H09-176165 discloses imidazopyridine derivatives having an ACAT inhibitory activity. WO93/25553 discloses imidazopyridine derivatives having an activity to treat atherosclerosis or hypercholesterolemia. U.S. Pat. No. 4,713,381 discloses imidazopyridine derivatives as reaction intermediates. However, all of these have a different structure from those of the compounds of the present invention. Further, these references do not disclose or imply a PI3K inhibiting and antitumor activity.

Hungarian patent publication No. HU 43066A2 and Eur. J. Med. Chem. (1989), 24(1), 97-9 discloses imidazopyridine derivatives substituted by a substitited-amino-substituted-1,3,5-triazinyl group having a cardiotonic activity. Arch. Pharm. (Weinheim, Ger.) (1992), 325(9), 623-4 discloses imidazopyridine derivatives substituted by a substitited-amino-substituted-1,3,4-oxadiazolyl which are useful as anticonvulsants. Moreover, the Maybridge catalogue (order No. SPB-04848) discloses imidazopyridine derivatives substituted by an alkylthio-substituted-pyrimidinyl group.

SUMMARY OF THE INVENTION

The present inventors have performed extensive investigations on compounds with a PI3K inhibiting activity. As a result, it has been discovered that novel imidazopyridine derivatives have an excellent PI3K inhibiting activity and cancer cell growth inhibiting activity. Based on the discovery, it has been found that the imidazopyridine derivatives could be excellent PI3K inhibitors and cancinostatic agents. The present invention has thus been achieved.

Therefore, the present invention relates to novel imidazopyridine derivatives or salts thereof which are useful as PI3K inhibitors and antitumor agents. The imidazopyridine derivatives are represented by the following general formula (I):

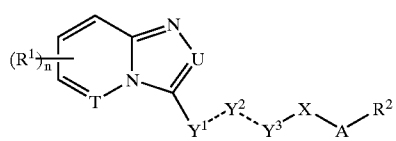

(I)

wherein $R^1$ represents —H, -a lower alkyl, -a lower alkenyl, -a lower alkynyl, -a cycloalkyl, -a cycloalkenyl, -a halogen, —$NO_2$, —CN, -a halogenated lower alkyl, —$OR^a$, —$SR^a$, —$SO_2R^a$, —$SOR^a$, —$CO_2R^a$, —CO—$R^a$, -an aryl, -a lower alkylene-an aryl, —O-a lower alkylene-an aryl, —$CONR^aR^b$, —CO-(a nitrogen-containing saturated heterocyclic group which may be substituted by a lower alkyl group), —$SO_2NR^aR^b$, —$SO_2$-(a nitrogen-containing saturated heterocyclic group which may be substituted by a lower alkyl group), —$SO_3H$, -(a nitrogen-containing saturated heterocyclic group which may be substituted by a lower alkyl group), —$NR^aR^b$, —$CONR^a$-a lower alkylene-$OR^b$, —$CONR^a$-a lower alkylene-$NR^bR^c$, —$CONR^a$-a lower alkylene-(a nitrogen-containing saturated heterocyclic group which may be substituted by a lower alkyl group), —O-a lower alkylene-$OR^a$, —O-a lower alkylene-O-a lower alkylene-$O^a$, —O-a lower alkylene-$NR^aR^b$, —O-a lower alkylene-(a nitrogen-containing saturated heterocyclic group which may be substituted by a lower alkyl group), —O-a lower alkylene-O-a lower alkylene-$NR^aR^b$, —O-a lower alkylene-O-a lower alkylene-(a nitrogen-containing saturated heterocyclic group which may be substituted by a lower alkyl group), —O-a lower alkylene-$NR^c$-a lower alkylene-$NR^aR^b$, —O-a lower alkylene-$NR^c$-a lower alkylene-(a nitrogen-containing saturated heterocyclic group which may be substituted by a lower alkyl group), —OCO—$NR^aR^b$, —OCO-(a nitrogen-containing saturated heterocyclic group which may be substituted by a lower alkyl group), —$NR^a$—$SO_2R^b$, —$NR^c$-a lower alkylene-$NR^aR^b$, —$NR^c$-a lower alkylene-(a nitrogen-containing saturated heterocyclic group which may be substituted by a lower alkyl group), —N(a lower alkylene-$NR^aR^b$)$_2$, —N(a lower alkylene-(a nitrogen-containing saturated heterocyclic group which may be substituted by a lower alkyl group))$_2$, —$CONR^a$—$OR^b$, —$NR^a$—$COR^b$, —$NR^aCO$—$NR^bR^c$, —$NR^a$—CO-(a nitrogen-containing saturated heterocyclic group which may be substituted by a lower alkyl group), or —$OCOR^a$;

$R^a$, $R^b$ and $R^c$ which may be the same or different, represent —H, -a lower alkyl or -an aryl;

T represents N or $CR^{1a}$;

U represents N or $CR^3$;

n represents an integer, 1, 2 or 3;

in Y . . . $Y^2$ . . . $Y^3$, i) . . . represents a single bond on one side and a single or double bond on the other side, $Y^1$ represents $CR^5$ or $CR^{5a}R^{5b}$, $Y^2$ represents N, NH, $CR^{4a}$ or $CR^{4b}R^{4c}$, and $Y^3$ represents N $R^6$, $CR^{4d}$ or $CR^{4e}R^{4f}$, whereas $Y^3$ represents $NR^6$ when $Y^2$ represents $CR^{4a}$ or $CR^{4b}R^{4c}$, or, ii) $Y^1$ and $Y^3$ may be bonded with each other via 2 or 3 atoms and combined with the adjacent $Y^2$ to form a B ring, wherein the B ring represents a 5- or 6-membered monocyclic heteroaryl ring having 1 to 4 hetero atoms selected from the group consisting of N, S, and O, a nitrogen-containing saturated heterocyclic ring or an aryl ring, whereas said B ring may be substituted by one to two $R^4$s;

X represents S, SO or $SO_2$, whereas X may also represent CO, $NR^7$ or a methylene group when $Y^1$ and $Y^3$ are bonded with each other via 2 or 3 atoms and combined with the adjacent $Y^2$ to form the B ring;

"A" represents a linkage, a lower alkylene, a lower alkenylene or a lower alkenylene;

$R^2$ represents -a lower alkyl which may have one or more subsituents, -a lower alkenyl which may have one or more subsituents, -a lower alkynyl which may have one or more subsituents, -a cycloalkyl which may have one or more subsituents, -a cycloalkenyl which may have one or more subsituents, —N═O, -an aryl which may have one or more subsituents, or -a heteroaryl which may have one or more subsituents;

$R^{1a}$, $R^3$, $R^{4a}$, $R^{4c}$, $R^{4d}$, $R^{4e}$, $R^{4f}$, $R^{5a}$, and $R^{5b}$, which may be the same or different, represent a group defined by $R^1$, whereas $R^{4b}$ and $R^{4c}$, $R^{4e}$ and $R^{4f}$, or $R^{5a}$ and $R^{5b}$ may be combined with each other to form an oxo group (═O);

$R^4$ represents a group defined by $R^1$, or an oxo group (═O);

$R^5$, $R^6$, and $R^7$, which may be the same or different, represent —H, -a lower alkyl which may have one or more subsituents, -a lower alkenyl which may have one or more subsituents, -a lower alkynyl which may have one or more subsituents, with proviso that when X is $NR^7$ and $R^2$ is an aryl having a substituent at the ortho-position, $R^7$ may be combined with the substituent at the ortho-position to form a $C_{2-3}$ lower alkylene chain, and with the aryl of $R^2$ to form a 5- to 7-membered nitrogen-containing heterocyclic ring fused with a benzene ring(s) of the aryl group;

with the proviso that
(1) X represents a group other than $NR^7$ when $Y^1$ . . . $Y^2$ . . . $Y^3$ is bonded with X via N atom or $Y^1$ and $Y^3$ are bonded with each other via 2 or 3 atoms and combined with the adjacent $Y^2$ to form a 1,3,5-triazine or 1,3,4-oxadiazole ring; and
(2) X represents SO, $SO_2$, CO or a methylene group when $Y^1$ and $Y^3$ are bonded with each other via 2 or 3 atoms and combined with the adjacent $Y^2$ to form a pyrimidine ring.

The present invention further relates to novel pharmaceutical compositions, particularly to PI3K inhibitors and anti-tumor agents, comprising an imidazopyridine derivative of formula (1) above or a salt thereof and a pharmaceutically acceptable carrier.

A further aspect of the present invention relates to treatment methods of disorders (especially cancers) influenced by PI3K, wherein an effective amount of a novel imidazopyridine derivative of formula (1) above or a salt thereof is administered to humans or animals.

EMBODIMENTS

The compounds of general formula (I) are described below in more detail.

The term "lower" throughout the specification is used to mean a straight or branched hydrocarbon chain having 1 to 10, preferably 1 to 6, and more preferably 1 to 3 carbon atoms.

Preferred examples of the "lower alkyl" are an alkyl having 1 to 6 carbon atoms, more preferably methyl and ethyl. Preferred examples of the "lower alkenyl" include vinyl, allyl, 1-propenyl, isopropenyl, 1-butenyl, 2-butenyl and 3-butenyl. Preferred examples of the "lower alkynyl" include ethynyl, 1-propynyl, 2-propynyl, 1-butynyl, 2-butynyl, 3-butynyl and 1-methyl-2-propynyl. Examples of the "cycloalkyl" and "cycloalkenyl" are preferably a cycloalkyl and a cycloalkenyl, each having 3 to 8 carbon atoms, more preferably cyclopropyl, cyclopentyl, cyclohexyl and cyclopentenyl. Preferred examples of the "lower alkylene" include methylene, ethylene, trimethylene and 2,2-dimethyltrimethylene. The "lower alkenylene" is preferably vinylene. The "lower alkenylene" is preferably ethynylene.

The term "aryl" is used throughout the specification to mean an aromatic cyclic hydrocarbon group. An aryl having 6 to 14 carbon atoms is preferable. It may be partially saturated. Preferred examples of such aryl are phenyl and naphthyl. When $Y^1$ and $Y^3$ are bonded via 2 or 3 atoms and combined with the adjacent $Y^2$ to form a B ring, a preferred aryl ring of the B ring is a benzene and naphthalene ring.

The "heteroaryl" throughout the specification includes a 5- or 6-membered monocyclic heteroaryl having 1 to 4 hetero atoms selected from the group consisting of N, S and O as well as a bicyclic heteroaryl in which such a monocyclic heteroaryl is fused to a benzene ring. The heteroaryl may be partially saturated. A 5- to 6-membered monocyclic heteroaryl having 1 to 4 hetero atoms selected from the group consisting of N, S, and O is preferably exemplified by groups of furyl, thienyl, pyrolyl, imidazolyl, pyrazolyl, thiazolyl, isothiazolyl, oxazolyl, isoxazolyl, triazolyl, tetrazolyl, thiadiazolyl, pyridyl, pyrimidinyl, pyridazinyl, and pyrazinyl. Examples of the bicyclic heteroaryl are preferably benzofuranyl, benzothienyl, benzothiadiazolyl, benzothiazolyl, benzimidazolyl, indolyl, isoindolyl, indazolyl, quinolyl, isoquinolyl, cinnolinyl, quinazolinyl, quinoxalinyl and benzodioxolyl. Specific examples of the partially saturated heteroaryl are 1,2,3,4-tetrahydroquinolyl, etc. Particularly preferred as a heteroaryl in $R^2$ are thienyl, pyrazolyl, thiazolyl, isoxazolyl, pyridyl, benzothiadiazolyl and quinolyl.

A "5- to 6-membered monocyclic heteroaryl ring having 1 to 4 hetero atoms selected from the group consisting of N, S, and O" in a B ring formed by bonding $Y^1$ with $Y^3$ via 2 or 3 atoms and combining $Y^1$ and $Y^3$ with the adjacent $Y^2$ is a heteroaryl ring forming the aforementioned "5- to 6-membered monocyclic heteroaryl having 1 to 4 hetero atoms selected from the group consisting of N, S, and O". Preferable examples are a furan, thiophene, pyrrole, imidazole, pyrazole, thiazole, isothiazole, oxazole, isoxazole, triazole, tetrazole, thiadiazole, pyridine, pyrimidine, pyridazine and pyrazine ring. More preferable examples are a 5-membered monocyclic heteroaryl ring. Among them, more preferable examples are a pyrrole, imidazole, pyrazole, thiazole, oxazole and triazole ring, and particularly preferable examples are a pyrazole and thiazole ring.

Examples of the "halogen" are F, Cl, Br and I. Examples of the "halogenated lower alkyl" are the aforementioned lower alkyl groups which are further substituted by one or more halogen atoms described above, preferably —$CF_3$.

The "nitrogen-containing saturated heterocyclic group" throughout the specification is a 5- to 7-membered heterocyclic group containing one or two nitrogen atoms on the ring, which may further contain one O or S atom and may form a bridge structure. Preferred examples of such heterocyclic group are 1-pyrrolidinyl, 1-piperazinyl, piperidino and morpholino. The "5- to 7-membered nitrogen-containing heterocyclic ring fused with a benzene ring(s) of the aryl group" which is formed by combining $R^7$ "with the substituent at the ortho-position to form a $C_{2-3}$ lower alkylene chain, and with the aryl of $R^2$" "when X is $NR^7$ and $R^2$ is an aryl having a substituent at the ortho-position" includes the above defined "nitrogen-containing saturated heterocyclic group" fused with an aryl ring(s), preferably 1-pyrrolidinyl and piperidino fused with a benzene ring. The "nitrogen-containing saturated heterocyclic group" in the B ring formed by bonding $Y^1$ with $Y^3$ via 2 or 3 atoms and combining $Y^1$ and $Y^3$ with the adjacent $Y^2$ is preferably a pyrrolidine, imidazolidine or pyrazolidine ring and more preferably is a pyrrolidine ring.

The subsituents in the "lower alkyl which may have one or more subsituents", "lower alkenyl which may have one or more subsituents" and "lower alkynyl which may have one or more subsituents" are 1~5 subsituents selected from Group D below.

Group D: -a halogen, —$NO_2$, —CN, —OH, —O-a lower alkyl, —O-a halogenated lower alkyl, —SH, —S-a lower alkyl, —$SO_2$-a lower alkyl, —SO-a lower alkyl, —COOH, —COO-a lower alkyl, —CO-a lower alkyl, —$CONH_2$, —$NH_2$, —NH-a lower alkyl, —N(a lower alkyl)$_2$, -(a nitrogen-containing saturated heterocyclic group which may be substituted by a lower alkyl group), -an aryl, -a heteroaryl, -a cycloalkyl and -a cycloalkenyl. The same applies hereinafter.

The substituent(s) for "-a cycloalkyl which may have one or more subsituents", "-a cycloalkenyl which may have one or more subsituents", "-an aryl which may have one or more subsituents", and "-a heteroaryl which may have one or more subsituents" shown by $R^2$ are preferably -a lower alkyl which may have 1~5 substituents which are selected from Group D, -a lower alkenyl which may have 1~5 substituents which are selected from Group D, -a lower alkynyl which may have 1~5 substituents which are selected from Group D, -a cycloalkyl which may have 1~5 substituents which are selected from Group E, -a cycloalkenyl which may have 1~5 substituents which are selected from Group E, -a halogen, —$NO_2$, —CN, -a halogenated lower alkyl, —O-a halogenated lower alkyl, —OH, —O-a lower alkyl, —SH, —S-a lower alkyl, —$SO_2$-a lower alkyl, —SO-a lower alkyl, —COOH, —COO-a lower alkyl, —CHO, —CO-a lower alkyl, —$SO_3H$, —$Ar^1$, —O—$Ar^1$, —S—$Ar^1$, —CO—$Ar^1$, —$SO_2$—$Ar^1$, —SO—$Ar^1$, -a lower alkylene-$Ar^1$, —O-a lower alkylene-$Ar^1$, —$CONH_2$, —CONH-a lower alkyl, —CON(a lower alkyl)$_2$, —$SO_2NH_2$, —$SO_2$NH-a lower alkyl, —$SO_2$N(a lower alkyl)$_2$, —CO-(a nitrogen-containing saturated heterocyclic group which may be substituted by a lower alkyl group), —$SO_2$-(a nitrogen-containing saturated heterocyclic group which may be substituted by a lower alkyl group), -(a nitrogen-containing saturated heterocyclic group which may be substituted by a lower alkyl group), —$NH_2$, —NH-a lower alkyl, —N(a lower alkyl, —NHCO-a lower alkyl, —NHCO—$Ar^1$, —$NHSO_2$-a lower alkyl, —$NHSO_2$—$Ar^1$, -azido and —N═N—$Ar^1$, wherein Group E consists of -a lower alkyl, -a lower alkenyl, -a lower alkynyl and the substituents in said Group D, and wherein $Ar^1$ is an aryl or a heteroaryl which may have 1 to 5 substituents selected from Group E. The same applies hereinafter.

When "n" is 2 or 3, $R^1$ groups may be the same or different. When two $R^4$ groups exist, each $R^4$ group may be the same or different from each other.

$R^3$, $R^{4a}$, $R^{4b}$, $R^{4c}$, $R^{4d}$, $R^{4e}$, and $R^{4f}$ are preferably —H, —OH, or a lower alkyl. Alternatively, $R^{4b}$ and $R^{4c}$ may be combined with each other to form an oxo group (=O). As for $R^4$, -a lower alkyl, =O, —COOH, —COO-a lower alkyl, —CO-a lower alkyl or —SO$^3$H is preferred. As for $R^5$ and $R^7$, —H or a lower alkyl is preferred. As for $R^6$, —H, -a lower alkyl or alkenyl group is preferred, wherein the lower alkyl or alkenyl group may be substituted by a substituent(s) selected from —O-a lower alkyl, —S-a lower alkyl, —SO$_2$-a lower alkyl, —SO-a lower alkyl, —COOH, —COO-a lower alkyl, —CO-a lower alkyl, —CONH$_2$, —NH$_2$, —NH-a lower alkyl, —N(a lower alkyl)$_2$, -(a nitrogen-containing saturated heterocyclic group which may be substituted by a lower alkyl group) and -an aryl.

Preferred imidazopyridine derivatives of the present invention are compounds of formula (I) as below.

(1) Compounds in which $R^1$ is —H, -a lower alkyl, -a lower alkenyl, -a lower alkynyl, -a cycloalkyl, -a cycloalkenyl, -a halogen, —NO$_2$, —CN, -a halogenated lower alkyl, —OH, —O-a lower alkyl, —O-an aryl, —SH, —S-a lower alkyl, —SO$_2$-a lower alkyl, —SO-a lower alkyl, —COOH, —COO-a lower alkyl, —CO-a lower alkyl, an aryl, —CO-an aryl, -a lower alkylene-an aryl, —O-a lower alkylene-an aryl, —CONH$_2$, —SO$_2$NH$_2$, —SO$_3$H, -a nitrogen-containing saturated heterocyclic group, —NH$_2$, —NH-a lower alkyl or —N(a lower alkyl)$_2$; T is $CR^{1a}$; U is $CR^3$; in $Y^1$ $Y^2$ $Y^3$, i) represents a single bond on one side and a single or double bond on the other side, $Y^1$ represents $CR^5$ or $CHR^{5a}$, $Y^2$ represents N, $CR^{4a}$ or $CHR^{4b}$, and $Y^3$ represents $NR^7$, $CR^{4d}$ or $CHR^{4e}$, or ii) $Y^1$ and $Y^3$ may be bonded with each other via 2 or 3 atoms and combined with the adjacent $Y^2$ to form a B ring, wherein the B ring represents a 5- or 6-membered monocyclic heteroaryl ring having 1 to 4 hetero atoms selected from the group consisting of N, S, and O, or an aryl ring, whereas the B ring may be substituted by one to two $R^4$s; $R^2$ represents —H, -a halogenated lower alkyl, —N=O, -an aryl which may have one or more subsituents, or -a heteroaryl which may have one or more subsituents; $R^{1a}$, $R^3$, $R^4$, $R^{4a}$, $R^{4b}$, $R^{4d}$ and $R^{4e}$, which may be the same or different, represent a group defined by $R^1$; and $R^5$, $R^{5a}$, $R^6$ and $R^7$, which may be the same or different, represent —H or -a lower alkyl, with proviso that when X is $NR^7$ and $R^2$ is an aryl having a substituent at the ortho-position, $R^7$ may be combined with the substituent at the ortho-position to form a $C_{2-3}$ lower alkylene chain, and with the aryl of $R^2$ to form a 5- to 7-membered nitrogen-containing heterocyclic ring fused with a benzene ring(s) of the aryl group.

(2) Compounds in which n is 1 and $R^1$ represents -a lower alkyl, -a halogen, —CN, —NO$_2$, -a halogenated lower alkyl, —OR$^a$, —O-a lower alkylene-an aryl, —CO$_2$R$^a$, —CONR$^a$-a lower alkylene—OR$^b$, —CONR$^a$R$^b$, —CO-(a nitrogen-containing saturated heterocyclic group which may be substituted by a lower alkyl group), —CONR$^a$-a lower alkylene-NR$^b$R$^c$, —CONR$^a$-a lower alkylene-(a nitrogen-containing saturated heterocyclic group which may be substituted by a lower alkyl group) or -an aryl.

(3) Compounds in which "A" represents a linkage and $R^2$ represents an aryl which may have one or more subsituents or a heteroaryl which may have one or more subsituents.

(4) Compounds in which $R^2$ represents a phenyl which may have one or more substituents which are selected from the group consisting of -(a lower alkyl which may be substituted by —OH), -a lower alkenyl, -a halogen, —NO$_2$, —CN, -a halogenated lower alkyl, —O-a halogenated lower alkyl, —OH, —O-a lower alkyl, —CO-a lower alkyl, —SO$_2$-a lower alkyl, —COOH, —COO-a lower alkyl, —CONH$_2$, —SO$_2$NH$_2$, —CO-an aryl, —SO$_2$-an aryl, —NH$_2$, —NH-a lower alkyl, —N(a lower alkyl)$_2$, -(a nitrogen-containing saturated heterocyclic group which may be substituted by a lower alkyl group), —NHCO-a lower alkyl, -an aryl which may be substituted by 1~5 substituents selected from Group E, and -a heteroaryl which may be substituted by 1~5 substituents selected from Group E.

(5) Compounds in which T represents CH and U represents CH or C-(a lower alkyl).

(6) Compounds in which X represents SO$_2$.

(7) Compounds in which i) $Y^1$ ... $Y^2$ ... $Y^3$ represents $CR^5$=N—NR$^6$, $CR^{5a}R^{5b}$—NH—N$^6$, $CR^{5a}R^{5b}$—$CR^{4b}R^{4c}$—N$^6$, or ii) $Y^1$ and $Y^3$ of $Y^1$ ... $Y^2$ ... $Y^3$ are bonded with each other via 2 or 3 atoms and combined with the adjacent $Y^2$ to form a 5- or 6-membered monocyclic heteroaryl ring, wherein said 5- or 6-membered monocyclic heteroaryl ring may be substituted by one to two $R^4$s.

(8) Compounds in which a chain structure or a partial structure of a monocyclic heteroaryl ring in the group, $Y^1$ ... $Y^2$ ... $Y^3$, contains a frame which is represented by "C=N—N", "C=N—C" or "C—N=C", preferably "C=N—N".

(9) Compounds in which $Y^1$ ... $Y^2$ ... $Y^3$ represents $CR^5$=N—NR$^6$, $R^5$ represents —H or -a lower alkyl, and $R^6$ represents —H, or a lower alkyl or alkenyl which may be substituted by one or more substituents selected from a group consisting of —O-a lower alkyl, —S-a lower alkyl, —SO$_2$-a lower alkyl, —SO-a lower alkyl, —COOH, —COO-a lower alkyl, —CO-a lower alkyl, —CONH$_2$, —NH$_2$, —NH-a lower alkyl, —N(a lower alkyl)$_2$, -(a nitrogen-containing saturated heterocyclic group which may be substituted by a lower alkyl group), and -an aryl.

(10) Compounds in which $Y^1$ and $Y^3$ of $Y^1$ ... $Y^2$ ... $Y^3$ are bonded with each other via 2 or 3 atoms and combined with the adjacent $Y^2$ to form a 5-membered monocyclic heteroaryl ring which may be substituted by one to two $R^4$s selected from the group consisting of -a lower alkyl, —COOH, —COO-a lower alkyl, —CO-a lower alkyl and —SO$_3$H.

(11) Compound having an inhibition activity (IC$_{50}$) of 5 μM or less as determined by the method of the Melanoma cell growth inhibition test (Test example 3).

Among the compounds of the present invention, preferred ones are listed below: 3-(6-Bromo-2-methylimidazo[1,2-a]pyridin-3-yl)-1H-pyrazol-1-yl 2-methyl-5-nitrophenyl sulfone; 3-(6-bromoimidazo[1,2-a]pyridin-3-yl)-1H-pyrazol-1-yl 2-methyl-5-nitrophenyl sulfone; 2'-[(6-bromoimidazo[1,2-a]pyridin-3-yl)methylidene]-1',2-dimethyl-5-nitrobenzenesulfonohydrazide; 2'-[(6-bromoimidazo[1,2-a]pyridin-3-yl)methylidene]-2-ethyl-1'-methyl-5-nitrobenzenesulfonohydrazide; 3-({2-[(6-bromoimidazo[1,2-a]pyridin-3-yl)methylidene]-1-methylhydrazino}sulfonyl)4-methylbenzonitrile; 2'-[(6-fluoroimidazo[1,2-a]pyridin-3-yl)methylidene]-1',2-dimethyl-5-nitrobenzenesulfonohydrazide; 2-amino-2'-[(6-chloroimidazo[1,2-a]pyridin-3-yl)methylidene]-1'-methyl-5-nitrobenzenesulfonohydrazide; 2'-[(6-chloroimidazo[1,2-a]pyridin-3-yl)methylidene]-1'-methyl-5-nitro-2-(2,2,2-trifluoroethoxy)benzenesulfonohydrazide; 6-chloro-3-[2-(2-methyl-5-nitrobenzenesulfonyl)thiazol-4-yl]imidazo[1,2-a]pyridine; 6-bromo-3-{[(2-methyl-5-nitrobenzenesulfonyl)(2-morpholinoethyl)hydrazono]methyl}imidazo[1,2-a]pyridine; 6-chloro-3-{[(methyl)(2-methyl-5-nitrobenzenesulfonyl)hydrazono]methyl}imidazo[1,2-a]pyridine; 3-{[(methyl)(2-methyl-5-nitrobenzenesulfonyl)hydrazono]methyl}imidazo[1,2-a]pyridine-6-carbonitrile; 5-cyano-2'-[(6-fluoroimidazo[1,2-a]pyridin-3-yl)

methylidene]-1',2-dimethylbenzenesulfonohydrazide;
5-cyano-2'-[(6-cyanoimidazo[1,2-a]pyridin-3-yl)
methylidene]-1',2-dimethylbenzenesulfonohydrazide; 1'2-
dimethyl-2'-[(6-methylimidazo[1,2-a]pyridin-3-yl)
methylidene]-5-nitrobenzenesulfonohydrazide; 2'-[(6-
chloroimidazo[1,2-a]pyridin-3-yl)methylidene]-2-(1H-
imidazol-1-yl)-1'-methyl-5-nitrobenzenesulfonohydrazide;
2'-[(6-chloroimidazo[1,2-a]pyridin-3-yl)methylidene]-2-
dimethylamino-1'-methyl-5-nitrobenzenesulfonohydrazide;
and salts thereof.

The compounds of the present invention may be geometric isomers or tautomers depending upon the kind of substituents. The present invention also covers these isomers in separated forms and the mixtures thereof. Furthermore, some of the compounds may contain an asymmetric carbon in the molecule; in such a case isomers could be present. The present invention also embraces the mixtures of these optical isomers and the isolated forms of the isomers.

Some of the compounds of the invention may form salts. There is no particular limitation so long as the formed salts are pharmacologically acceptable. Specific examples of acid addition salts are salts with inorganic acids such as hydrochloric acid, hydrobromic acid, hydroiodic acid, sulfuric acid, nitric acid, phosphoric acid, etc., organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid, glutamic acid, etc. Specific examples of basic salts include salts with inorganic bases containing metals such as sodium, potassium, magnesium, calcium, aluminum, etc., or salts with organic bases such as methylamine, ethylamine, ethanolamine, lysine, ornithine, etc. The present invention further embraces various hydrates and solvates to the compounds (I) or salts thereof of the invention as well as polymorphism thereof (Processes for producing compounds)

Hereinafter representative processes for producing the compounds of the present invention are described below. In these processes, functional groups present in the starting materials or intermediates may be suitably protected with protective groups, depending upon the kind of functional groups. In view of the preparation technique, it may be advantageous to protect the functional groups with groups that can readily be reverted to the original functional groups. When required, the protective groups are removed to give the desired products. Examples of such functional groups are amino, hydroxy, carboxy, etc. Examples of the protective groups which may be used to protect these functional groups are shown in, e.g., Greene and Wuts, "Protective Groups in Organic Synthesis", second edition. These protective groups may be appropriately employed depending upon reaction conditions.

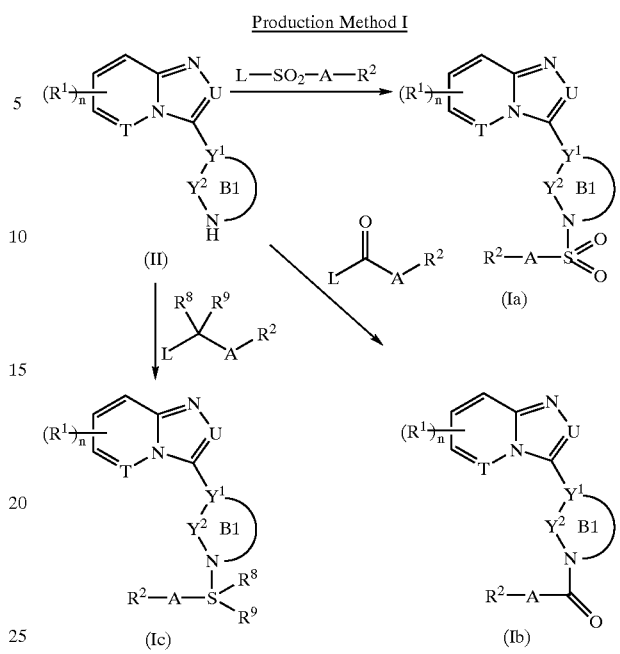

Production Method I (Here and hereinafter, the B 1 ring represents a 5- or 6-membered monocyclic heteroaryl ring having 1 to 4 hetero atoms selected from the group consisting of N, S, and O, or a nitrogen-containing saturated heterocyclic ring, said B ring may be substituted by one to two $R^4$s and $Y^3$ is an N atom; and L represents a leaving group.)

The compounds (Ia), (Ib), and (Ic) of the present invention may be prepared by subjecting heterocycle derivatives shown by general formula (II) to various modification reactions such as sulfonylation, amidation, and alkylation according to a conventional manner.

In the above formula, a leaving group shown by L is a halogen (fluorine, chlorine, bromine, iodine, etc.) or a sulfonyloxy group (e.g., methanesulfonyloxy, trifluoromethanesulfonyloxy, toluenesulfonyloxy, benzenesulfonyloxy, etc.), and preferably chlorine, bromine, iodine, and trifluoromethanesulfonyloxy. These leaving groups are appropriately selected depending on the kind of starting material or reaction.

Sulfonylation reaction may be performed by reacting heterocycle derivatives (II) with reactive derivatives of sulfonic acid according to a conventional manner. The reactive derivatives of sulfonic acid include sulfonyl chloride as a most ordinary example, as well as sulfonyl bromides, acid anhydrides (sulfonic anhydride prepared from two molecules of sulfonic acid), acid azides, and the like. Such reactive derivatives of sulfonic acid may be readily obtained from the corresponding sulfonic acid in a conventional manner. An example in which sulfonyl chloride is prepared includes a method described in J. Chem. Soc. Pak., 8(1), 11–17(1986), and Bull. Chem. Soc. Jpn., 59(2), 465–70 (1986). Alternative prepare sulfonyl chloride include a method in which chlorosulfonic acid is employed as a reaction agent, such as those described in Org. Synth., 1941, I, 85 or J. Med. Chem., 33(9), 2569–78(1990), and the Sandmeyer reaction via a diazonium salt as described in Tetrahedron Lett., 31(26), 3714–18(1990) or J. Am. Chem. Soc., 112(12), 4976–7(1990).

In the case of using acid halides as the reactive derivatives for sulfonylation, the sulfonylation is performed preferably in the presence of a base (an inorganic base such as sodium hydroxide, sodium hydride, etc., or an organic base such as pyridine, triethylamine (TEA), diisopropylethylarmine, etc.). When the pyrazole derivatives (II) are reacted with reactive derivatives such as acid anhydrides or acid azides, the sulfonylation may be carried out in the absence of a base. Alternatively, the reaction may be performed in the presence of a base such as sodium hydride, TEA, pyridine or 2,6-lutidine. The reaction temperature may be appropriately chosen depending on the kind of reactive derivatives used. As a solvent that may be used, there are basic solvents such as pyridine; an aromatic hydrocarbon solvent such as benzene or toluene; an ether solvent such as tetrahydrofuran (TEF), 1,4-dioxane, etc.; a halogenated hydrocarbon solvent such as dichloromethane, chloroform, etc.; an amide solvent such as N, N-dimethylformamide (DMF), N,N-dimethylacetamide, etc.; a carbonyl-based solvent such as acetone, methyl ethyl ketone, etc. These solvents may be used alone or as an admixture of two or more. The solvent should be appropriately chosen depending on the kind of starting compounds.

The amidation reaction may be performed in a conventional manner, preferably by converting carboxylic acid into reactive derivatives such as acid halides (acid chlorides, etc.) or acid anhydrides, and then reacting the reactive derivatives with the heterocycle derivatives (II). In the case of using reactive derivatives of carboxylic acid, the aforementioned base is preferably added. Further, amidation of the heterocycle derivatives (II) with carboxylic acids may be carried out in the presence of condensation agent (1-ethyl-3-(3-dimethylaminopropyl) carbodiimide (EDCI), 1,1'-carbonylbis-1H-imidazole (CDI), etc.). At this time, an additive such as 1-hydroxybenzotriazole (HOBt) or the like may be added. The reaction temperature may be appropri-ately chosen depending on the kind of starting compounds. As a solvent, an inert solvent to the reaction may be used, e.g. the solvent used in the above sulfonylation. These solvents may be used alone or as an admixture of two or more. The solvent should be chosen depending on the kind of starting compounds.

Alkylation may be performed in a conventional method, and preferably in the presence of the aforementioned base such as potassium carbonate, sodium hydroxide, sodium hydride, or the like. An alkylating agent such as alkyl halide or sulfonate (an ester of p-toluenesulfonic acid, an ester of trifluoromethanesulfonic acid, etc.) may be employed. The reaction may be conducted under cooling or heating or at room temperature. As a solvent, an inert solvent to the reaction may be used, e.g. the solvent used in the above sulfonylation. These solvents may be used alone or as an admixture of two or more. The solvent should be chosen depending on the kind of starting compounds. Further, when alkylation gives a monoalkylated compound, the compound can be converted to a dialkyl compound using a conventional alkylation reaction again. Moreover, when aldehydes or ketones are used as a reaction agent, reductive alkylation can be performed by using reducing agents such as sodium borohydride, sodium triacetoxyborohydride or sodium cyanoborohydride, dehydrator to give the corresponding imine and then reducing the imine by sodium borohydride. The reductive alkylation also can be performed by using a Dean—Stark.

The starting compounds (II), which are heterocycle derivatives, may be prepared in a conventional manner in accordance with the type of each heterocycle. Representative production methods are illustrated below:

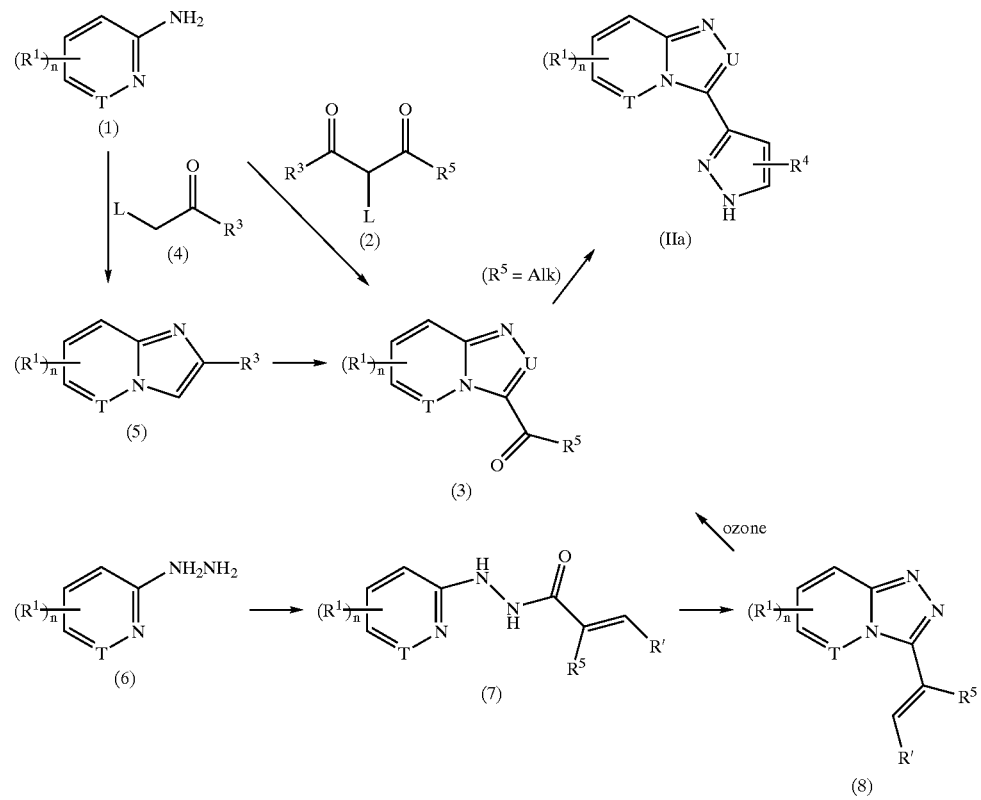

(Alk represents an alkyl group, and R' represents an alkyl or aryl group.)

The pyrazole derivatives (IIa) are synthesized by reacting acyl compounds (3) with N,N-dimethylformamide dimethylacetal, etc., to give dimethylamino-enone compounds and further adding hydrazine to the enone compounds for cyclization. The reaction may be conducted either in the absence of any solvent or in the presence of an organic solvent inert to the reaction. The reaction may be performed under cooling or heating or at room temperature. Acyl compounds (3) in which U represents $CR^3$ can be obtained by a reaction of amino compounds (1) with diketone compounds (2). It can be also obtained by a method in which a halogenated ketone alkylates N-pyridylamidine as described in Synthesis, 263–265 (1984). Alternatively, acyl compounds (3) can be obtained by an acylation reaction of Friedel-Crafts types to imidazopyridine derivatives (5). The acylation reaction may be performed in a conventional manner. For example, a method according to J. Med. Chem., 13, 1048 (1970) may be employed. The compound (5) may be easily prepared using aminopyridine derivatives (1) and α-halogenated carbonyl compounds (4) in a conventional manner.

Acyl compounds (3) in which U represents N can be obtained by oxidative cleavage of a double bond of olefin compounds (8), e.g., via ozonolysis. At the time, depending upon starting compounds and reaction conditions, ketone equivalents such as hemiketals may be separated. In these cases, such compounds can be changed to desired acyl compounds using appropriate reaction conditions. Olefin compounds (8) can be synthesized by heating hydrazides (7) in acetic acid as an example. Hydrazides (7) can be synthesized by acylation of hydrazines (6) in a conventional method.

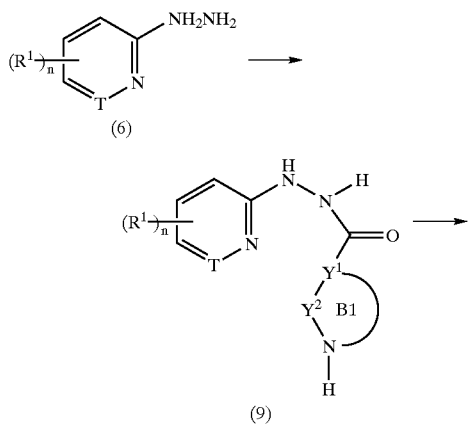

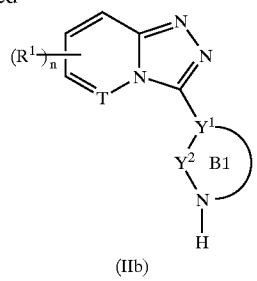

The starting compounds (IIb) can be synthesized by heating hydrazide compounds (9) in acetic acid as an example to cyclize them. Hydrazide compounds (9) can be synthesized by acylation of hydrazines (6) in a conventional method.

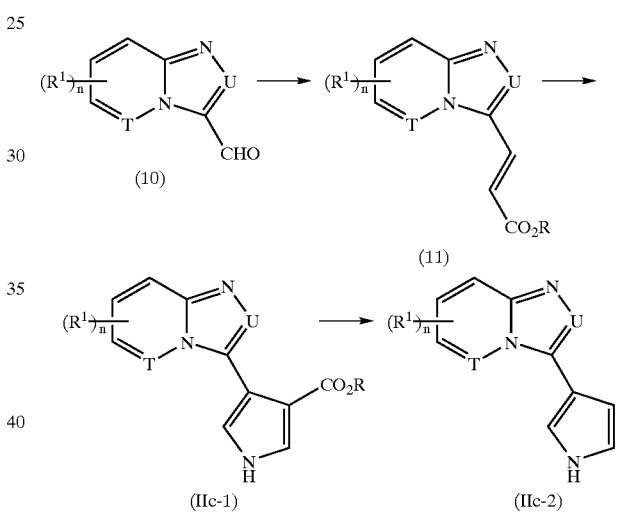

The starting compounds (IIc-1) can be synthesized by reacting enone compounds (11) with tosylmethylisocyanide (TosMIC) in a conventional method and compounds (11) can be synthesized by subjecting compounds (10) to the Homer-Emmons-Wadsworth reaction in a conventional method. As for compounds (10), the synthesis method of said compounds (3) can serve basically as a reference. Differences lie in that when U represents $C-R^3$, hormylation by the Vilsmeier reaction is employed instead of the acylation of compounds (5) and in that when diketone reacts with compounds (1) to create an imidazopyridine ring, halogenated malonoaldehyde is employed as a reaction agent. Examples of the Vilsmeier reaction includes a method described in the aforementioned J. Med. Chem., 13, 1048 (1970). When U represents N, compounds with $R^5$ representing H can be utilized in the synthesis of compounds (3) as the starting compounds to give compounds (10). The starting compounds (IIc-2) can be synthesized by subjecting ester compounds (IIc-1) to hydrolysis and decarboxylation with heating.

Production Method II

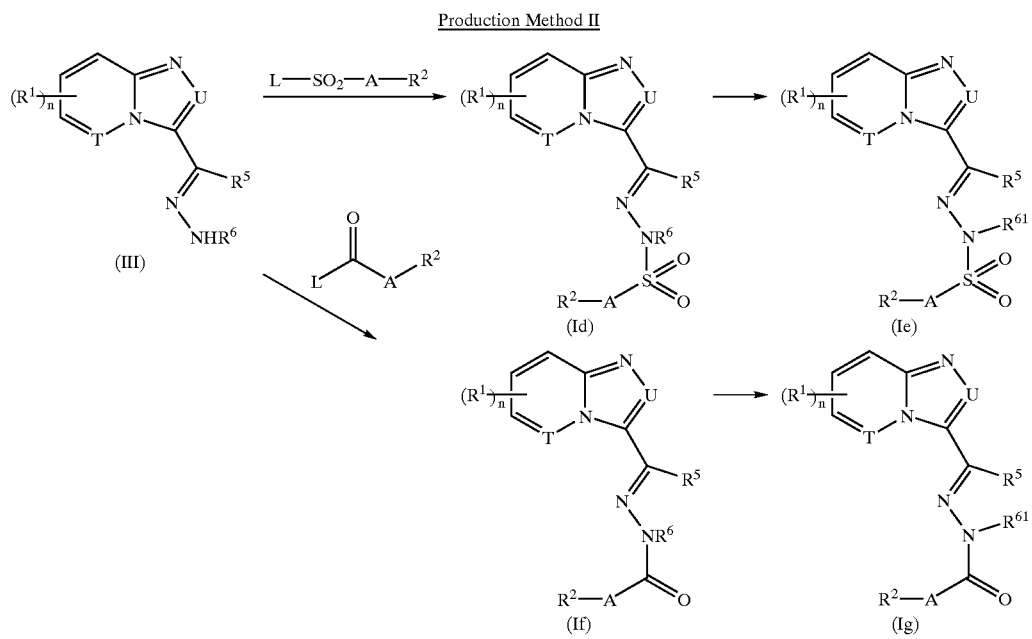

(Here and hereinafter, $R^{61}$ represents a group as defined for $R^6$, other than H.)

In this process, hydrazone derivatives shown by the formula (III) is subjected to various modification reactions such as sulfonylation or amidation according to a conventional manner to obtain compounds (Id) and (If) of the present invention. When $R^6$ represents H, the compounds (Id) and (If) of the present invention can be led to invented compounds (Ie) and (Ig) by known methods of a functional group transformation, such as alkylation, etc., as desired.

These sulfonylation, amidation, and alkylation may be conducted in the same manner as in the Production Method I.

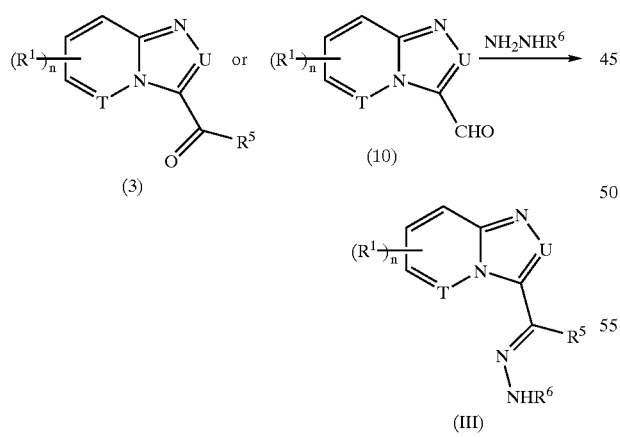

The starting compounds (III), which are hydrazone derivatives, may be synthesized in a conventional manner by reacting acyl compounds (3) or (10) with hydrazine compounds shown by $NH_2NHR^6$ or its hydrate, preferably in an alcohol solvent such as methanol or ethanol under cooling or heating or at room temperature.

Production Method III

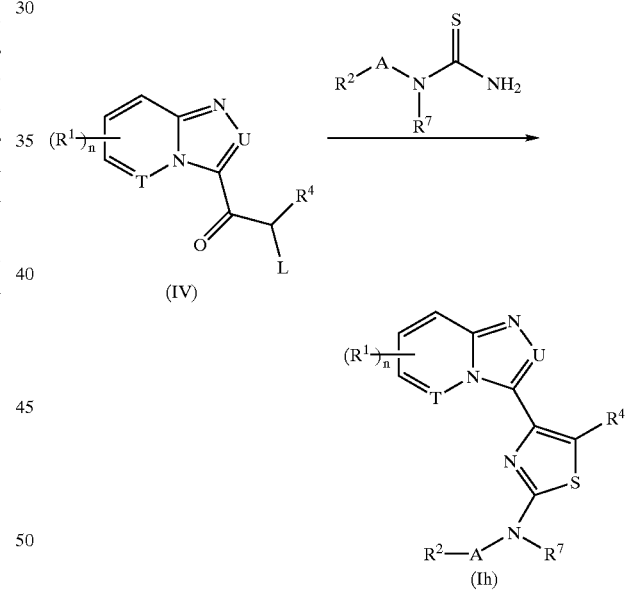

This is a process for obtaining aminothiazole derivatives (Ih) by subjecting α-halogenated ketone, etc., shown by a formula (IV) to a cyclization reaction with thiourea.

The cyclization reaction may be conducted in a conventional manner. For example, thiourea compounds or the like are reacted with α-halogenated ketone (IV) or the like in solvents or without any solvent under cooling or heating or at room temperature. Preferable solvents are alcohol solvents such as methanol, ethanol and isopropanol, the above carbonyl-based solvents, ether solvents, halogenated hydrocarbon solvents, amide solvents, etc. The solvent should be appropriately chosen depending on the kind of starting compounds, and these solvents may be used alone or as an admixture of two or more. The reaction sometimes proceeds smoothly by adding a base (potassium carbonate, sodium carbonate, TEA, etc.).

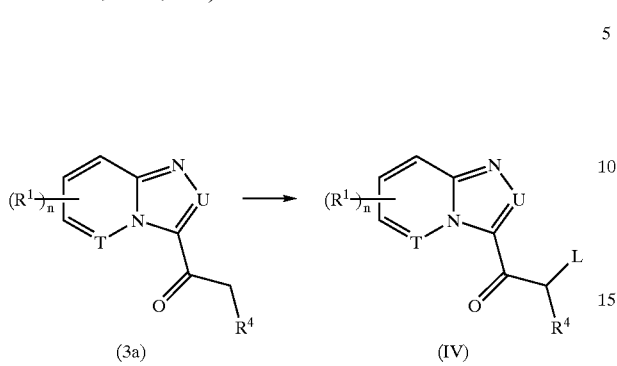

(3a) → (IV)

The starting compounds (IV), which are α-halogenated ketone derivatives, may be synthesized by halogenation of acyl compounds (3a) in a conventional manner. Halogenation reagents are, for example, chlorine, bromine, iodine, copper bromide (II), potassium iodate, benzyltrimethylammonium tribromide, phenyltrimethylammonium tribromide, tetrabutylamnmonium tribromide, sulfuryl chloride, trimethylsilyl chloride, trimethylsilyl bromide, and 5,5-dibromobarbituric acid. As a solvent, a solvent inert to the reaction may be used, for example, acidic solvents such as acetic acid and hydrobromic acid/acetic acid, the aforementioned alcohol solvents and ether solvents. The reaction temperature may be under cooling or heating or at room temperature.

The desired starting compound may also be prepared by appropriately known methods to convert substituents, wherein proper methods may depend on the kind of substituents.

Production Method IV

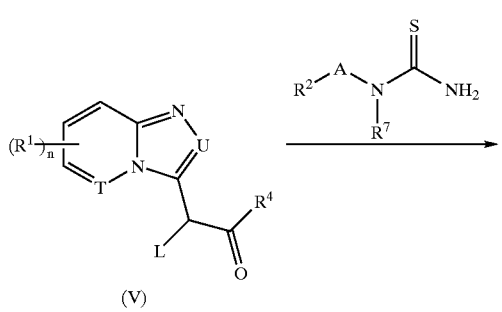

(V)

-continued

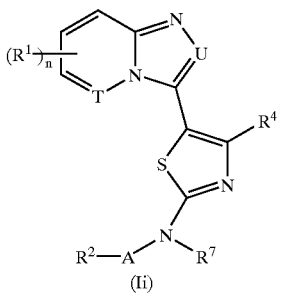

(Ii)

This is a process for obtaining a compound (Ii) of the present invention by subjecting α-halogenated ketone, etc., shown by a formula (V) to a cyclization reaction with thiourea. The cyclization reaction may be performed in the same manner as in Production Method III. The starting compound (V) may be synthesized in the same manner as the starting compound (IV).

Production Method V

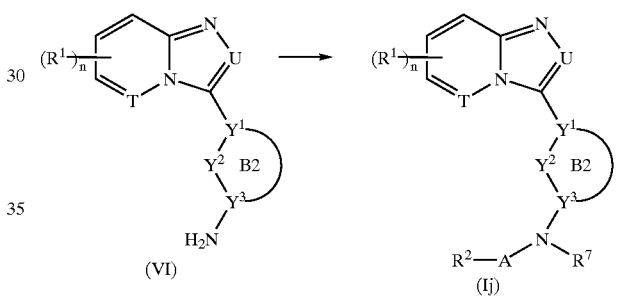

(VI) → (Ij)

(Here and hereinafter, the B2 ring represents a 5- or 6-membered monocyclic heteroaryl ring having 1 to 4 hetero atoms selected from the group consisting of N, S, and O, a nitrogen-containing saturated heterocyclic ring, a nitrogen-containing saturated heterocyclic group or an aryl ring, whereas said B2-ring may be substituted by one to two $R^4$s and $Y^3$ is a C atom.)

This process is for obtaining a compound (Ij) of the present invention by subjecting amino compounds shown by the formula (V) to an alkylation or arylation reaction. The alkylation reaction may be performed in a conventional manner, for example, the same manner as that in Production Method I. Further, known converting methods such as N-alkylation or the like may be appropriately performed. Examples of the arylation reaction include coupling reactions described in Acc. Chem. Res., 31, 805, (1998) and ibid. 31, 852 (1998) and ipso-substitution described in J. Org. Chem., 63(18), 6338(1998). The starting amino compounds (VI) can be synthesized according to a conventional method. For example, when the B2-ring is an imidazole, they can be synthesized using the aforementioned α-halogenated ketone (IV) as a starting material in a conventional method, for example, a method described in J. Org. Chem. 59(24) 7299–7305 (1994). When the B2-ring is a thiazole ring, they can be produced by reacting unsubstituted thiourea as a reaction agent according to the method described in the aforementioned Production Method IV.

Production Method VI

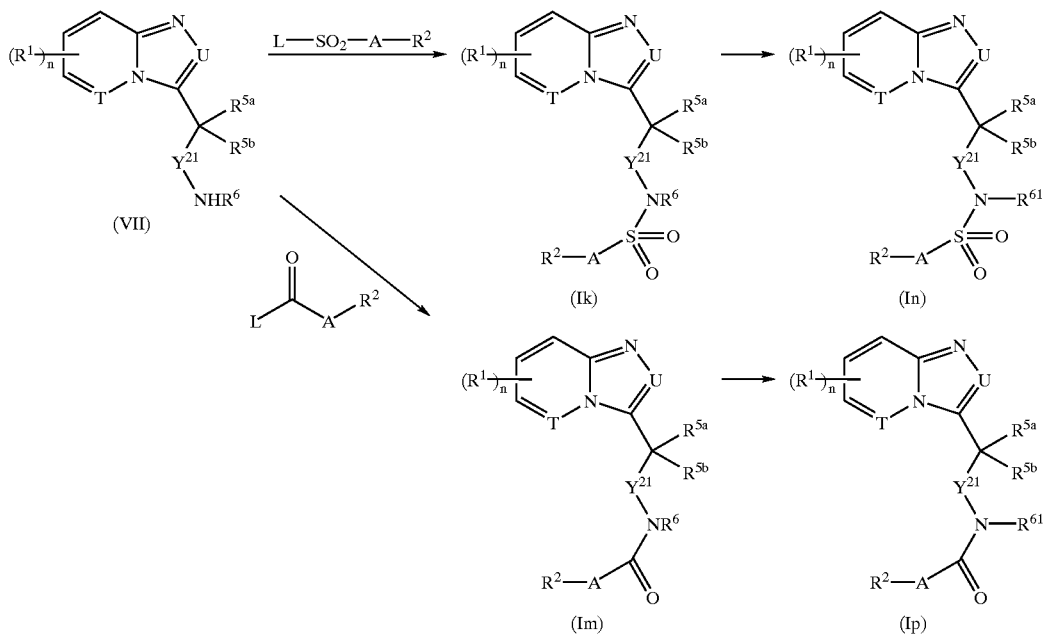

(Here and hereinafter, $Y^{21}$ represents NH or $CR^{4a}R^{4b}$.)

This process is for synthesizing compounds (Ik) and (Im) of the present invention by subjecting amine derivatives shown by the formula (VII) to various modification reactions of sulfonylation and amidation according to conventional methods. Further, the compounds (Ik) and (Im) of the present invention can be led to compounds (In) and (Ip) of the present invention, respectively, by known methods of a substituent conversion, such as alkylation or the like. Sulfonylation, amidation, and alkylation can be conducted, for example, in the same manner as in Production Method I. The starting compounds (VI) can be readily sythensized using the methods shown by the synthetic routes below as an example.

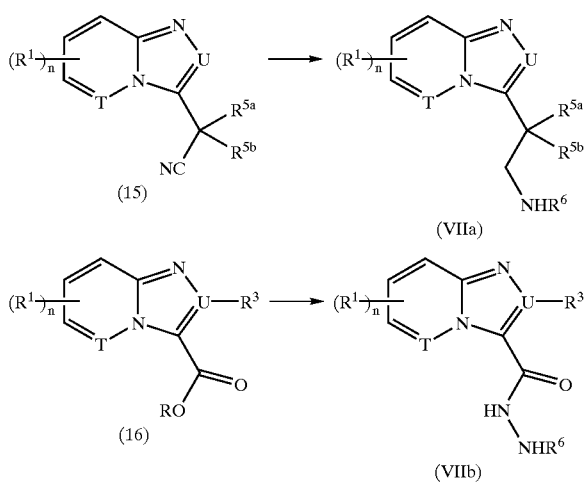

-continued

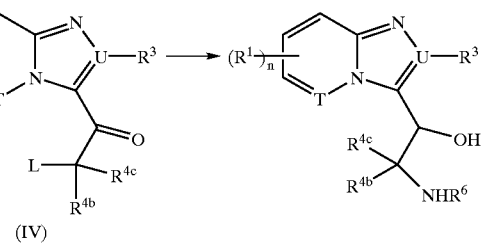

The starting material (VIIa) can be readily synthesized, as an example, by subjecting the nitrile compounds (15) to reducing reactions described in Jikken Kagaku Kouza (Encyclopedia for Experimental Chemistry) edited by Nihon Kagaku Kai (Japanese Association of Chemistry) and published by Maruzen Co., Ltd. The nitrile compounds (15) can be produced by subjecting the aforementioned acyl compounds (3) to a conventional method such as one described in J. Med. Chem. 12, 122 (1969). The compounds (VIIb) can be synthesized by reacting the ester compounds (16) with hydrazines at room temperature or under heating. The compounds (VIIc) can be synthesized by reducing α-halogenated ketone derivatives (IV) with an agent such as sodium borohydride to give epoxide or halohydrin compounds, followed by the treatment with amino compounds.

Production Method VII

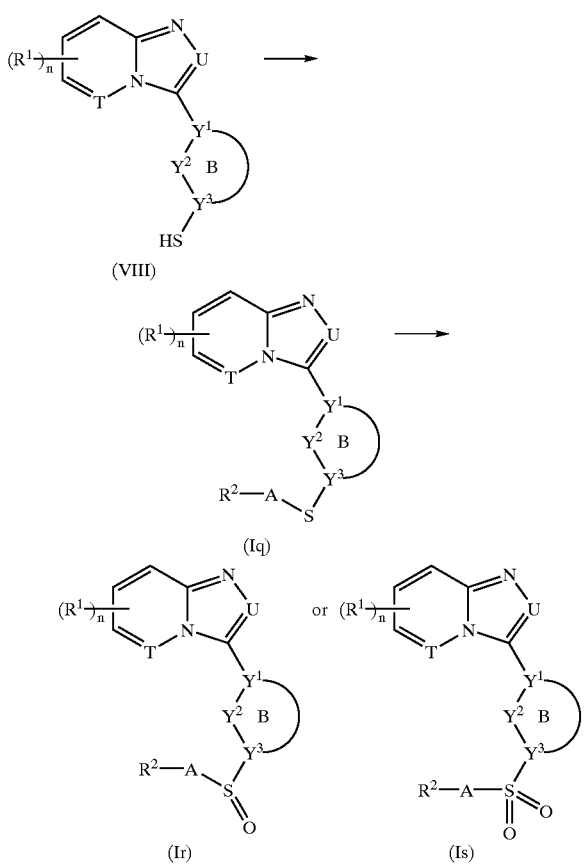

(Here and hereinafter, the B ring represents a 5- or 6-membered monocyclic heteroaryl ring having 1 to 4 hetero atoms selected from the group consisting of N, S, and O, a nitrogen-containing saturated heterocyclic ring, an aryl ring, whereas the B ring may be substituted by one to two $R^4$s.)

This process is for converting thiol compounds (VIII) to the compounds of the present invention (Iq) and conducting an oxidation reaction as necessary to synthesize sulfoxide derivatives and sulfone derivatives shown by the formula (Ir) and (Is). Examples of methods to synthesize sulfide compounds (Iq) from the starting materials, thiol compounds (VIII), include a method in which reacting them with halogenated alkyl or halogenated aralkyl in the presence of a base according to a conventional method when the group, —A—$R^2$, is an alkyl or aralkyl. When the group, —A—$R^2$, is an aryl or heteroaryl, sulfide compounds (Iq) can be obtained by a coupling reaction with an halogenated aryl. For the coupling reaction, for example, a method according to J. Org. Chem. 1993, 58(12), 3229–3230, and Synth Commun. 1982, 12(13), 1071 may be used when the halogen is fluorine, a method according to Synthesis 11, 892 (1981) may be used when the halogen is bromine, and a method according to Chem. Lett. 11, 1363 (1980) may be used when the halogen is iodine. Moreover, a method can be employed in which the thiolate salts (VIII) are reacted with diazonium salts, and an ipso-substitution reaction can be so employed in which an aryl group having appropriate leaving groups is subjected to thiolate salts at room temperature or under heating. As for the reaction conditions, methods can be referenced which are described, for example, in Japanese patent KOKAI (Laid—Open) No. 2000-53635 and Tetrahedron Lett., 26, 6365 (1985).

The oxidation reaction to convert (Iq) to (Ir) and (Is) may be performed according to a conventional method, and an oxidizing agent such as m-chloroperoxybenzoic acid, hydrogen peroxide, peracetic acid, potassium permanganate, oxone and sodium periodate may be used. In case with compounds which are not easily oxidized, the reaction conditions, for example, described in J. Heterocyclic Chem., 28, 577 (1991) and Tetrahedron Lett., 35, 4955 (1994) may be referenced. In the case that a functional group other than the aimed sulfide is oxidized and, for example, converted to an oxidant such as N-oxide upon the oxidation reaction, it can be deoxidized with an appropriate reducing agent according to a conventional manner.

The starting compounds (VIII) may be synthesized according to conventional methods. For example, when the B ring is a heteroaryl, the methods for thiazol described in Bioorganic & Medicinal Chemistry, 5, 601 (1997) and J. Org. Chem., 13, 722 (1948), those for imidazole described in J. Am. Chem. Soc., 71, 4000 (1949), J. Indian Chem. Soc., 52(12), 1117 (1981) and Chem. Pharm. Bull., 32(7), 2536 (1984), those for oxazole described in Fr1450443 (1965), JCS Perkin Trans. 1,3, 435 (1984), Chem. Pharm. Bull., 40, 245 (1992) and Bull. Soc. Chim. Belges., 70, 745 (1961); and those for thiadiazole described in Chem. Ber., 94, 2043 (1961) may be referenced for their synthesis. Compounds with other rings can be synthesized by constructing a B ring by methods described in, for example, "Comprehensive Heterocyclic Chemistry" edited by Katritzky, Rees, "The Chemistry of Heterocyclic Compounds" edited by A. Weissberger, and E. C. Taylor, or "Advanced in Heterocyclic Chemistry" edited by A. R. Katritzky.

Production Method IX

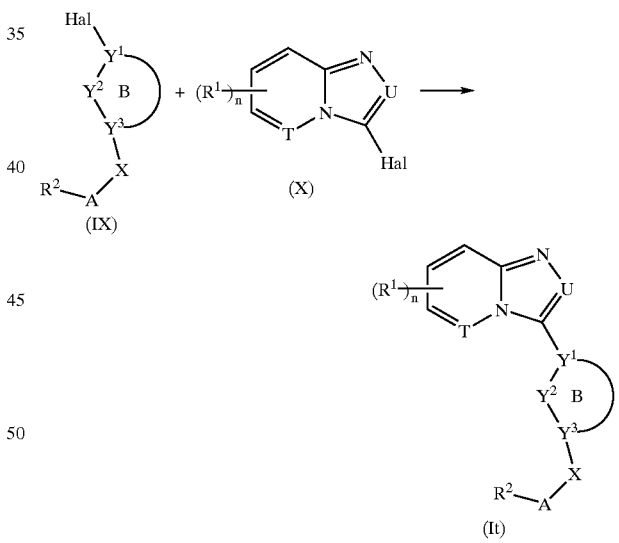

(Here, Hal represents a halogen.)

This process is for converting halogenated aryl compounds shown by the formula (IX) and (X) by a coupling reaction according to a conventional manner to the compounds (It) of the present invention. The coupling reaction can be conducted according to a conventional method. The coupling reaction is preferably performed in the presence of a catalyst such as palladium, nickel or copper after (IX) or (X) is converted to a reactive derivative such as an aryl metal reagent, an arylboronic acid derivative or an aryl tin compound in a conventional manner. An example of these coupling reactions is a method described in Jikken Kagaku Kouza as described hereinbefore. The starting compounds (IX) may be synthesized by constructing a B ring by methods described in, for example, "Comprehensive Heterocyclic Chemistry", "The Chemistry of Heterocyclic Compounds" or "Advanced in Heterocyclic Chemistry" as described hereinbefore, and then by employing, as necessary, the alkylation reaction, coupling reaction, oxidizing reaction, deoxygenation reaction which are described in Production Method VII.

The desired compound of the present invention may also be prepared by functional group transformation methods well known to those skilled in the art, which may depend on the kind of the substituent. The order of the reactions, or the like, may be appropriately changed in accordance with the aimed compound and the kind of reaction to be employed.

The other compounds of the present invention and starting compounds can be easily produced from suitable materials in the same manner as in the above processes or by methods well known to those skilled in the art.

Each of the reaction products obtained by the aforementioned production methods is isolated and purified as a free base or a salt thereof. The salt can be produced by a usual salt forming method. The isolation and purification are carried out by employing usually used chemical techniques such as extraction, concentration, evaporation, crystallization, filtration, recrystallization, various types of chromatography and the like.

Various forms of isomers can be isolated by the usual procedures making use of physicochemical differences among isomers. For instance, racemic compounds can be separated by means of a conventional optical resolution method (e.g., by forming diastereomer salts with a conventional optically active acid such as tartaric acid, etc. and then optically resolving the salts) to give optically pure isomers. A mixture of diastereomers can be separated by conventional means, e.g., fractional crystallization or chromatography. In addition, an optical isomer can also be synthesized from an appropriate optically active starting compound.

INDUSTRIAL APPLICABILITY

The compounds of the present invention exhibit a kinase inhibitory activity, especially PI3K inhibitory activity and therefore, can be utilized in order to inhibit abnormal cell growths in which PI3K plays a role. Thus, the compounds are effective in the treatment of disorders with which abnormal cell growth actions of PI3K are associated, such as restenosis, atherosclerosis, bone disorders, arthritis, diabetic retinopathy, psoriasis, benign prostatic hypertrophy, atherosclerosis, inflammation, angiogenesis, immunological disorders, pancreatitis, kidney disease, cancer, etc. In particular, the compounds of the present invention possess excellent cancer cell growth inhibiting effects and are effective in treating cancers, preferably all types of solid cancers and malignant lymphomas, and especially, leukemia, skin cancer, bladder cancer, breast cancer, uterus cancer, ovary cancer, prostate cancer, lung cancer, colon cancer, pancreas cancer, renal cancer, gastric cancer, brain tumor, etc.

The pharmacological effects of the compounds accordingto the invention have been verified by the following pharmacological tests.

Test Example 1 Inhibition of PI3K (p110α Subtype)

Inhibition was determined using enzyme (bovine p110α) prepared in the baculovirus expression system. Bovine p110α was prepared according to a modification from the method by I. Hiles et al., Cell, 70, 419 (1992). Each compound to be assayed was dissolved in dimethylsulfoxide (DMSO) and the obtained 10 mM DMSO solution was serially diluted with DMSO. The compound (0.5 μl) to be assayed and enzyme were mixed in 25 μl of buffer solution (40 mM Tris-HCl (pH 7.4), 200 mM NaCl, 2 mM dithiothreitol, 5 mM $MgCl_2$). Then, 25 μl of 5 mM Tris-HCl (pH 7.4) buffered solution supplemented with 10 μg PI (Sigma), 2 μCi[γ-$^{32}$P] ATP (Amersham Pharmacia) and 80 μM non-radiolabeled ATP (Sigma) was added to the mixture to initiate the reaction. After reacting at 37° C. for 15 minutes, 200 μl of 1M HCl and 400 μl of $CHCl_3$/MeOH (1:1) were added to the reaction mixture. The resulting mixture was stirred and then centrifuged. After the organic layer was extracted twice with 150 μl of MeOH/1M HCl (1:1). The radioactivity was measured using Cerenkov light.

The $IC_{50}$ inhibition activity was defined by a 50% inhibition concentration of each compound assayed, which was converted from the radioactivity determined as 100% when DMSO alone was added and as 0% when no enzyme was added.

The compounds of the present invention showed excellent inhibitory activities. For example, Compound 6 of the present invention inhibits PI3K more than 10 times as strong as known PI3K inhibitor LY294002.

Test Example 2 Colon Cancer Cell Growth Inhibition

HCT116 cells from a colon cancer cell line were cultured in McCoy's 5A medium (GIBCO) supplemented with 10% fetal bovine serum. HCT116 cells were inoculated on a 96 well plate (5000 cells/well) followed by overnight incubation. The test compound diluted with the medium was added to the medium in a final concentration of 0.1 to 30 μM (final DMSO concentration, 1%). After incubation for over 72 hours, Alamar Blue reagent was added to the medium. Two hours after the addition, a ratio of fluorescent intensity at an excitation wavelength of 530 nm to that at an emission wavelength of 590 nm was measured to determine the $IC_{50}$.

Compounds 5, 6, 8, and 9 of the present invention exerted a good cancer cell growth inhibition activity.

Test Example 3 Melanoma Cell Growth Inhibition

A375 cells from a melanoma cell line were cultured in DMEM medium (GIBCO) supplemented with 10% fetal bovine serum. A375 cells at 10,000 cells/100 μl were added to a 96 well plate which contained 1 μl/well of the test compounds (final concentration of 0.001~30 μM). After incubation for over 46 hours, Alamar Blue reagent was added to the medium (10 μl/well). Two hours after the addition, a ratio of fluorescent intensity at an excitation wavelength of 530 nm to that at an emission wavelength of 590 nm was measured to determine the $IC_{50}$ of the test compounds in the same manner as in the above examples.

Compounds 6, 30, 43, 53, 54, 57, 59, 60, 65, 77, 88, 93, 95, 96, 99, 112 and 113 of the present invention exerted a good melanoma cell growth inhibition activity. Their $IC_{50}$ values were less than 1 μM. Contrarily, the known PI3K inhibitor LY294002 showed a value of 8.39 μM.

In addition to the above cancer cell lines, the compounds of the present invention exhibited excellent cancer cell growth inhibiting activities against Hela cells from a cervix cancer cell line, A549, H460 cells from a lung cancer cell line, COLO205, WiDr, Lovo cells from a colon cancer cell line, PC3, LNCap cells from a prostate cancer cell line, SKOV-3, OVCAR-3, CH1 cells from an ovary cancer cell line, U87 MG cells from a glioma cell line and BxPC-3 cells from a pancreas cancer cell line.

Test Example 4 In Vivo Anti-tumor Activities

A single-cell suspension of HelaS3 (5×10$^6$ cells), a human cervix cancer cell line, was inoculated into the flank of female Balb/c nude mice by subcutaneously injection. When the tumor reached 100~200 mm$^3$ in volume, test compounds were intraperitoneally administered once a day for two weeks. 20% Hydroxypropyl-β-cyclodextrin/saline was intraperitoneally administered with the same schedule as a control group. The diameter of the tumors was measured with a vernier caliper at certain time intervals until one day after the final doze administration. The tumor volume was calculated by the following formula: 1/2×(a shorter diameter)$^2$×(a longer diameter).

In the present test, test compounds exhibited superior anti-tumor activities as compared with the control group.

The pharmaceutical composition of the present invention can be prepared in a conventional manner by mixing one or more compounds of the invention shown by general formula (I) with a carrier for medical use, a filler and other additives usually used in pharmaceutical preparations. The pharmaceutical composition of the invention may be administered either orally in the form of tablets, pills, capsules, granules, powders, liquid, etc., or parenterally such as by intravenous or intramuscular injection, in the form of suppositories, or through pemasal, permucosal or subcutaneous route.

For oral administration of the composition in the present invention, a solid composition in the form of, e.g., tablets, powders or granules is available. In such a solid composition, one or more active or effective ingredients are blended with at least one inert diluent such as lactose, mannitol, glucose, hydroxypropyl cellulose, microcrystalline cellulose, starch, polyvinyl pyrrolidone or magnesium aluminate metasilicate. The composition may further contain additives other than the inert diluent by the usual procedures. Examples of such additives include a lubricant such as magnesium stearate, a disintegrating agent such as calcium cellulose glycolate, a solubilization assisting agent such as glutaric acid or aspartic acid. Tablets or pills may be coated, if necessary, with films of sugar or a gastric or enteric substance such as sucrose, gelatin, hydroxypropyl cellulose, hydroxypropylmethyl cellulose phthalate, etc.

A liquid composition for oral administration includes pharmaceutically acceptable emulsions, solutions, suspensions, syrups, elixirs, etc. and contains an inert diluent conventionally employed, e.g., purified water or ethanol. In addition to the inert diluent above, the liquid composition may further contain an auxiliary agent such as a moistening agent or a suspending agent, a sweetener, a flavor and/or a preservative.

A composition for parenteral administration contains a sterile aqueous or non-aqueous solution, a suspension and an emulsion. Examples of the aqueous solution and suspension include distilled water for injection use and physiological saline. Typical examples of the non-aqueous solution and suspension are propylene glycol, polyethylene glycol, vegetable oil such as olive oil, an alcohol such as ethanol, polysorbate 80, and the like. These compositions may further contain a preservative, a moistening agent, an emulsifier, a dispersing agent, a stabilizer and a solubilization assisting agent. These compositions are sterilized, e.g., by filtering them through a bacteria retention filter, incorporating a bactericide or through irradiation. Alternatively, they may be prepared into a sterile solid composition, which is dissolved in sterile water or a sterile solvent for injection prior to use.

In the case of oral administration, suitable daily does is usually about 0.0001 to 50 mg/kg body weight, preferably about 0.001 to 10 mg/kg, more preferably about 0.01 to 1 mg/kg, and the daily does is administered once a day or divided into 2 to 4 doses per day. In the case of intravenous injection, suitable daily dose is usually about 0.0001 to 1 mg/kg body weight, preferably about 0.0001 to 0.1 mg/kg. And the daily dose is administered once a day or divided into a plurality of doses per day. The dose may be appropriately determined for each case, depending on conditions, age, sex, etc.

The compounds of the present invention can be utilized alone, or in conjunction with other treatments (e.g., radiotherapy and surgery). Moreover, they can be utilized in conjunction with other antitumor agents, such as alkylation agents (cisplatin, carboplatin, etc.), antimetabohites (methotrexate, 5-FU, etc.), antitumor antibiotics (adriamymycin, bleomycin, etc.), antitumor vegetable alkaloids (taxol, etoposide, etc.), antitumor hormones (dexamethasone, tamoxifen, etc.), antitumor immunological agents (interferon α, β, γ, etc.), and so forth.

TABLE 1

| Rco | Str | Dat | Rco | Str | Dat |
|---|---|---|---|---|---|
| a1 | [structure: 6-bromo-imidazo[1,2-a]pyridine with 2-Me and 3-C(=O)Me] | N1: 2.59(3H, s), 2.72(3H, s), 9.74(1H, m) | a2 | [structure: 6-methyl-imidazo[1,2-a]pyridine with 2-Me and 3-C(=O)Me] | N2: 2.60(3H, s), 2.77(3H, s), 6.85(1H, m) |
| a3 | [structure: imidazo[1,2-a]pyridine with 2-Me and 3-C(=O)Me] | N2: 2.63(3H, s), 2.80(3H, s), 9.75(1H, m) | a4 | [structure: 8-OBn-imidazo[1,2-a]pyridine with 2-Me and 3-C(=O)Me] | F: 281 |

TABLE 1-continued

| Rco | Str | Dat | Rco | Str | Dat |
|---|---|---|---|---|---|
| a5 | | F: 209 | a6 | | F: 189 |
| b1 | | N2: 2.58(3H, s), 2.77(3H, s), 9.94(1H, m) | c1 | | N1: 2.56(3H, s), 6.70(1H, m), 7.32(1H, m) |
| c2 | | N1: 2.37(3H, s), 6.81(1H, m), 7.31(1H, s) | c3 | | F: 305 |
| c4 | | N1: 2.53(3H, s), 6.95(1H, m), 7.27(1H, m) | c5 | | F: 275 |
| c6 | | F: 233 | c7 | | F: 213 |
| c8 | | N1: 8.10(1H, s), 9.65–9.70(1H, m), 13.16(1H, brs) | d1 | | F: 213 |

TABLE 2
| | | | | | |
|---|---|---|---|---|---|
| e1 | 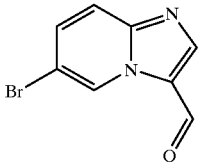 | N1: 8.56(1H, s), 9.51(1H, s), 9.96(1H, s) | f1 | 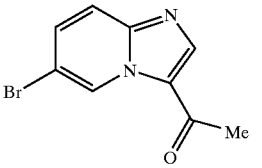 | N2: 2.62(3H, s), 8.28–8.33(2H, m), 9.83(1H, m) |
| g1 | 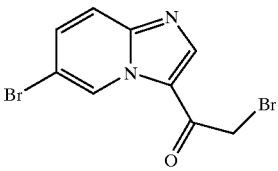 | N1: 4.83(2H, s), 8.94(1H, s), 9.63(1H, s) | g2 | 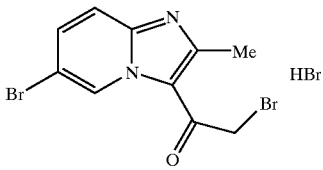 | N1: 2.81(3H, s), 4.87(2H, s), 9.76(1H, s) |
| g3 | 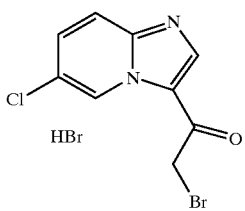 | F; 275 | g4 | 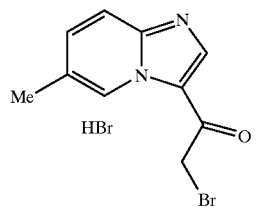 | F; 253, 255 |
| h1 | 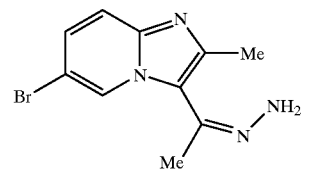 | N1: 2.17(3H, s), 6.57(2H, brs), 9.31(1H, d, J=1.5Hz) | i1 | 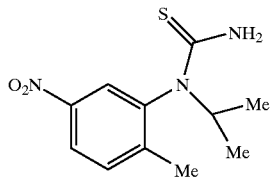 | N2: 0.96(3H, d, J=6.8Hz), 1.38 (3H, d, J=6.8Hz), 2.37(3H, s) |
| j1 | 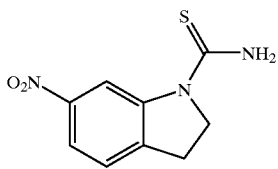 | N1: 3.23(2H, t, J=8.3Hz), 4.17(2H, t, J=8.3Hz), 7.46(1H, d, J=7.8Hz) | j2 | 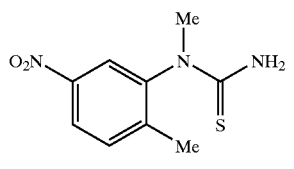 | F: 226 |
| k1 | 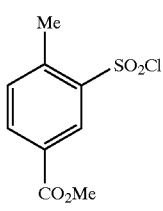 | N1; 2.59(3H, s), 3.85(3H, s), 8.33(1H, d, J=2.0Hz). | m1 | 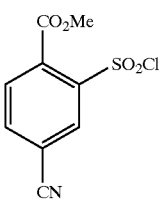 | N1; 3.76(3H, s), 7.53(1H, d, J=6.0Hz), 8.06 (1H, s). |
| m2 | 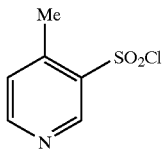 | N1; 2.83(3H, s), 7.99(1H, J=6.0Hz), 8.92 (1H, s). | m3 | 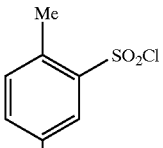 | N2; 2.88(3H, s), 7.59(1H, d, J=8.0Hz), 8.36 (1H, d, J=2.0Hz). |
| m4 | 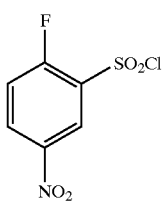 | N1; 7.47(1H, t, J=9.0Hz), 8.25–8.32(1H, m), 8.47(1H, dd, J=6.0, 3.0Hz). | n1 | 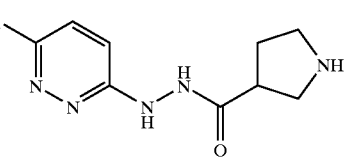 | E; 237 |

TABLE 2-continued

| | | |
|---|---|---|
| n2 | 6-chloropyridazine-N'H-NH-C(O)-pyrrolidine-N-Boc | FN; 340 |
| n3 | 5-chloropyridine-NH-NH-C(O)-CH=CH-Ph | FN; 272 |

TABLE 3

| | | |
|---|---|---|
| n4 | 6-chloropyridazinyl-NH-NH-C(O)-C6H4-S-CH2-C6H4-OMe | FN; 399 |
| n5 | 6-chloropyridazinyl-NH-NH-C(O)-CH=CH-Ph | FN; 273 |
| p1 | 6-chloro-[1,2,4]triazolo[4,3-b]pyridazine with pyrrole | F; 220 |
| p2 | 6-chloro-[1,2,4]triazolo[4,3-b]pyridazine with N-Boc-pyrrolidine | F; 324 |
| q1 | 6-chloro-[1,2,4]triazolo[4,3-b]pyridazine-3-CHO | N2; 757(1H, dd J=9.5, 2.0Hz), 7.98 (1H, dd, J= 9.5, 1.0Hz), 9.33(1H, dd, J=2.0, 1.0Hz). |
| r1 | 6-chloro-[1,2,4]triazolo[4,3-b]pyridazine-3-CH(OH)(OMe) | N1; 3.43(3H,s), 6.06(1H, d, J=7.5 Hz), 8.47 (1H, d, J= 9.5Hz) |

TABLE 3-continued
| s1 | 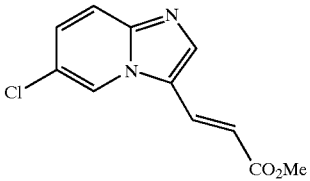 | F; 237 |
| t1 | 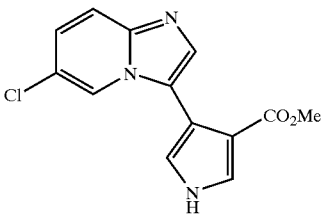 | F; 276 |
| u1 | 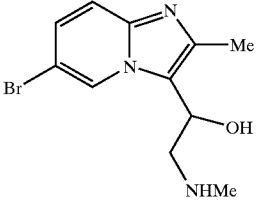 | N2; 2.27(3H, s), 2.39(3H, s), 8.90–9.05 (1H, m) |
| v1 | 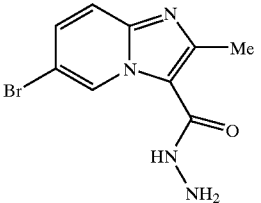 | F; 269, 271 |
| w1 | 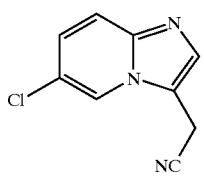 | F; 192 |
| x1 | 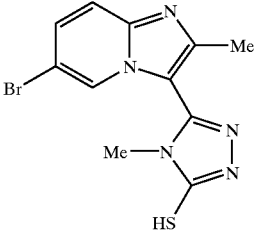 | F; 324, 326 |
| y1 | 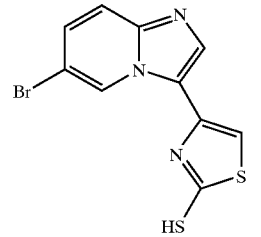 | F; 312, 314 |

TABLE 3-continued

| | | |
|---|---|---|
| y2 | [6-Cl imidazo[1,2-a]pyridine-3-yl, 2-mercapto-thiazol-4-yl] | F; 268 |
| y3 | [6-Me imidazo[1,2-a]pyridine-3-yl, 2-mercapto-thiazol-4-yl] | F; 253, 255 |
| b2 | [6-Ph imidazo[1,2-a]pyridine-3-yl, CHO] | FN; 272 |

TABLE 4

Structure (I): imidazo[1,2-a]pyridine (positions 5,6,7,8; R$^1$ on 6/7) with 2-Me, 3-(1-sulfonyl-pyrazol-3-yl), R$^2$-SO$_2$-

| Co | R$^1$ | R$^2$ | Syn | Dat |
|---|---|---|---|---|
| 1 | H | phenyl | 1 | N2: 6.91(1H, t, J=6.8Hz), 7.56(2H, t, J=7.8Hz), 8.08(2H, d, J=8.3Hz) |
| 2 | 7-Me | 3-cyanophenyl (NC-) | 1 | N1: 7.08(1H, d, J=6.4), 7.48(1H, s)8.67(1H, t, J=1.4) |
| 3 | H | 4-bromophenyl | 1 | N2: 6.94(1H, t, J=6.8Hz), 7.69(2H, d, J=9.3Hz), 7.93(2H, d, J=8.7Hz) |
| 4 | 6-Cl | 4-fluorophenyl | 1 | M: 195–196; N1: 2.54(3H, s), 7.09(1H, d, J=2.9Hz), 8.73(1H, d, J=2.9Hz) |
| 5 | 6-Cl | 3-nitrophenyl (O$_2$N-) | 1 | M: 217–218; N1: 2.58(3H, s), 7.13(1H, d, J=2.9Hz), 7.66(1H, d, J=9.3Hz) |
| 6 | 6-Br | 4-nitro-3-methylphenyl (O$_2$N-, Me) | 1 | M: 202–203; N1: 2.56(3H, s), 2.76(3H, s), 7.13(1H, d, J=2.9Hz) |
| 7 | 6-Cl | thiophen-2-yl | 1 | M: 216–217; N1: 2.57(3H, s), 7.08(1H, d, J=2.9Hz), 8.69(1H, d, J=2.9Hz) |
| 8 | 6-Cl | 4-nitro-3-methylphenyl (O$_2$N-, Me) | 1 | M: 207–208; N1: 2.55(3H, s), 2.769(3H, s), 7.13(1H, d, J=2.9Hz) |

TABLE 4-continued

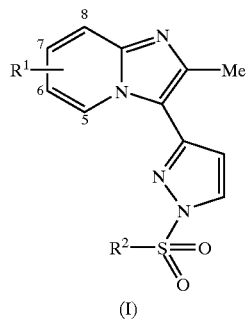

(I)

| Co | R¹ | R² | Syn | Dat |
|----|-----|-----|-----|-----|
| 9 | 6-Cl | NC-(3-methylphenyl) | 1 | M: 196–197; N1: 2.54(3H, s), 7.65(1H, d, J=9.7Hz), 8.76(1H, d, J=2.9Hz) |
| 10 | 6-Br | 2-methylthiophene | 1 | M: 210–211; N1: 2.56(3H, s), 7.08(1H, d, J=2.9Hz), 8.69(1H, d, J=2.9Hz) |

TABLE 4-continued

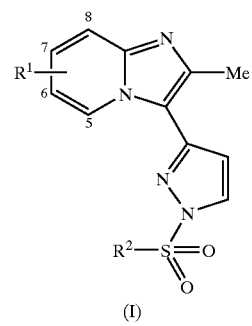

(I)

| Co | R¹ | R² | Syn | Dat |
|----|-----|-----|-----|-----|
| 11 | 6-Br | Me | 1 | M: 217–218; N1: 2.60(3H, s), 3.67(3H, s), 7.07(1H, d, J=2.9Hz) |
| 12 | H | 4-fluorophenyl | 1 | F: 357; N1: 2.55(3H, s), 7.06(1H, d, J=3.0Hz), 8.69(1H, d, J=3.0Hz) |

TABLE 5

(I)

| Co | R¹ | R² | | R⁴ | Syn | Dat |
|----|-----|-----|---|-----|-----|-----|
| 13 | 6-Br | -(4-MeO-Ph) | | H | 1 | F: 447; HPLC: 15.5 |
| 14 | 6-Ph | -(4-NH₂-Ph) | | H | 1 | F: 430; HPLC: 15.3 |
| 15 | 6-Cl | (4-AcNH-Ph) | | H | 1 | F: 430; HPLC: 15.1 |
| 16 | H | -(3,5-CF₃-Ph) | | H | 1 | F: 475; HPLC: 18.3 |
| 17 | 6-Me | -Naph | | H | 1 | F: 403; HPLC: 17.4 |
| 18 | 8-Me | 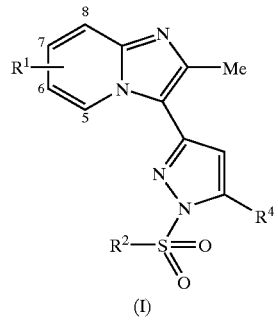 | | H | 1 | F: 418; HPLC: 14.9 |
| 19 | 6-Me | 4,5-dimethyl-2-acetamidothiazole | | H | 1 | F: 431; HPLC: 15.5 |
| 20 | 6-Cl | -(4-CF₃O-Ph) | | H | 1 | F: 457; HPLC: 19.6 |

TABLE 5-continued (Structure I: Imidazo[1,2-a]pyridine with R¹ substituent, 2-Me group, connected to pyrazole bearing R²-SO₂- on N1 and R⁴ at position 5)

| Co | R¹ | R² | R⁴ | Syn | Dat |
|---|---|---|---|---|---|
| 21 | 6-Cl | 5-Cl-1,4-dimethyl-3-methyl-pyrazol-yl | H | 1 | F: 425; HPLC: 16.8 |
| 22 | 6-Cl | benzo[1,2,5]thiadiazol-4-yl | H | 1 | F: 431; HPLC: 15.9 |
| 23 | 6-Cl | 3,5-dimethyl-4-methyl-isoxazol-yl | H | 1 | F: 392; HPLC: 17.2 |
| 24 | 6-Cl | -(4-CH₂=CH-Ph) | H | 1 | F: 399; HPLC: 13.3 |
| 25 | 6-Cl | —CH=CH-Ph | H | 1 | F: 399; HPLC: 17.3 |
| 26 | 8-O-CH₂-Ph | 4-(phenylazo)-phenyl (with Me) | Me | 1 | F: 563; HPLC: 23.5 |
| 27 | 6-Cl | 5-(dimethylamino)-naphthalen-1-yl | H | 1 | F: 466; HPLC: 20.8 |
| 28 | 6-Cl | 2-chloro-6-(4-methylphenoxy)-3-cyanophenyl | H | 1 | F: 524; HPLC: 17.6 |
| 29 | 6-Me | 5-methyl-thiophen-2-yl phenylsulfonyl | H | 1 | F: 499; HPLC: 15.1 |

TABLE 6

[Structure (I): 6-bromo-imidazo[1,2-a]pyridine with R³ at 2-position and Y-X-aryl(2-Me, 5-NO₂) at 3-position]

| Co | R³ | -Y- | X | Sal | Syn | Dat |
|---|---|---|---|---|---|---|
| 30 | H | 1-methylpyrazol-3-yl | SO₂ | — | 1 | M: 195–196<br>N1: 2.80(3H, s), 7.31(1H, d, J=2.9Hz), 8.35(1H, s) |
| 31 | Me | 1-methylpyrazol-3-yl | CO | — | 2 | N1: 2.63(3H, s), 7.24(1H, d, J=2.9Hz), 7.76(1H, d, J=8.3Hz) |
| 32 | Me | —C(Me)=N—NH— | SO₂ | — | 3 | N1: 2.39(3H, s), 2.79(3H, s), 11.41(1H, brs) |
| 33 | Me | 2-methylthiazol-4-yl | NH | HBr | 4 | N1: 2.68(3H, s), 9.44(1H, s), 10.07(1H, s) |
| 34 | H | —C(Me)=N—NH— | SO₂ | — | 5 | M: 197–198(dec)<br>N1: 2.41(3H, s), 2.79(3H, s), 11.40(1H, brs) |
| 35 | H | 2-methylthiazol-4-yl | N(iPr) | HCl | 6 | M: 164–166<br>N1: 2.37(3H, s), 4.55(1H, sep, J=6.9 Hz), 9.55(1H, s) |
| 36 | Me | —C(Me)=N—N(Me)- | SO₂ | — | 7 | N1: 2.63(3H, s), 2.66(3H, s), 2.71(3H, s), 3.01(3H, s) |
| 39 | Me | 2-methylthiazol-4-yl | N(Me) | HBr | 4 | M: 248–252(dec)<br>N1: 2.39(3H, s), 2.68(3H, s), 3.51(3H, s) |
| 40 | H | 2-methylthiazol-4-yl | N(Me) | HBr | 4 | N1: 2.38(3H, s), 3.53(3H, s), 9.53(1H, s) |
| 41 | H | —CH=N—NH— | SO₂ | — | 5 | M: 185–186<br>N1: 2.77(3H, s), 8.31(1H, s), 12.20(1H, brs) |
| 42 | H | —C(Me)=N—N(Me)- | SO₂ | — | 7 | M: 216–220<br>N1: 2.63(3H, s), 2.72(3H, s), 3.02(3H, s) |
| 43 | H | —CH=N—N(Me)- | SO₂ | — | 7 | M: 204–205<br>N1: 2.69(3H, s), 3.47(3H, s), 8.31(3H, s) |
| 44 | Me | —C(Me)=N—N(Bn)- | SO₂ | — | 7 | M: 175–177<br>N1: 2.27(3H, s), 2.54(3H, s), 2.67(3H, s), 4.52(2H, s) |

TABLE 7
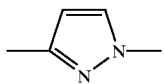
(I)
| Co | R³ | -Y- | X | R² | Sal | Syn | Dat |
|---|---|---|---|---|---|---|---|
| 37 | Me | 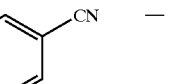 | $CH_2$ | 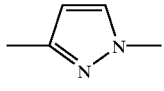 | — | 8 | M: 235–238; N1: 2.53(3H, s), 5.57 (2H, s), 6.72(1H, d) J=2.4Hz) |
| 38 | Me | 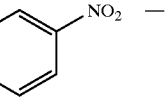 | CO | 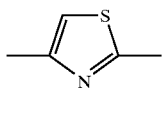 | — | 9 | M: 154–157; 1: 2.63(3H, s), 4.87(2H, s), 7.14(1H, d, J=2.9Hz) |
| 45 | Me | 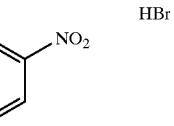 | — | 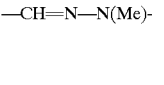 | HBr | 4 | M: 271–273(dec); N1: 2.71(3H, s), 3.49(2H, t, J=8.3Hz), 4.25(2H, t, J=8.3Hz) |
TABLE 8
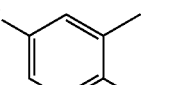
(I)
| Co | R³ | -Y- | -R² | Sal | Syn | Dat |
|---|---|---|---|---|---|---|
| 46 | H | —CH=N—N(Me)- | 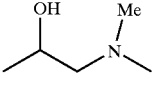 | HCl | 10 | M: 205–208; N1: 2.69(3H, s), 3.48 (3H, s), 8.74(1H, d, J=2.4Hz) |
| 47 | Me | 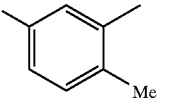 |  | — | 11 | N1: 4.15(2H, m), 5.18(2H, m), 8.28(1H, s) |
| 48 | H | —CH₂CH₂NH— | 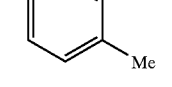 | HCl | 12 | M: 221–223 |
| 49 | H | 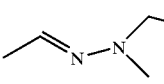 | 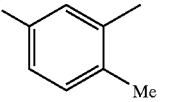 | HCl | 13 | M: 199–201; N1: 2.68(3H, s), 8.80 (1H, d, J=2.5Hz), 9.15(1H, s). |
| 50 | H | —CH=N—N(Me)- | 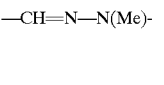 | HCl | 14 | M: 191–193; N1: 2.63(3H, s), 3.46 (3H, s), 3.87(3H, s). |

TABLE 8-continued

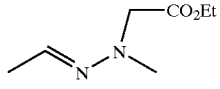

(I)

| Co | R³ | -Y- | -R² | Sal | Syn | Dat |
|---|---|---|---|---|---|---|
| 51 | H | —CH=N—N(Me)- | NaO₂C-C₆H₃(Me)- (Mw) | — | 15 | M: 235(dec); N1: 2.59(3H, s), 3.35 (3H, s), 7.35(1H, d). |
| 52 | H | —CH=N—N(Me)- | H₂NOC-C₆H₃(Me)-Me | HCl | 16 | M: 200(dec); N1: 2.61(3H, s), 3.45 (3H, s), 7.56(1H, s). |
| 53 | H | —CH=N—N(Me)- | O₂N-C₆H₃(Me)-Et | HCl | 17 | M: 208–211; N1: 3.45(1H, s), 8.20 (1H, s), 8.32(1H, s). |
| 54 | H | —CH=N—N(Me)- | NC-C₆H₃(Me)-Me | HCl | 18 | M: 208–210; N1: 2.65(3H, s), 3.47 (3H, s), 9.26(1H, s). |
| 71 | H | =N-N(Me)-CH₂-CO₂Et | O₂N-C₆H₃(Me)-Me | — | 10 | M: 200–201 |

TABLE 9

| 72 | Me | —CONHNH— | O₂N-C₆H₃(Me)-Me | — | 11 | N1: 2.88(3H, s), 10.44(1H, brs), 10.67(1H, brs) |
| 73 | Me | —CONHNMe- | O₂N-C₆H₃(Me)-Me | — | 13 | N1: 2.82(3H, s), 8.81(1H, brs), 10.32(1H, brs) |
| 74 | H | —CH₂CH₂NMe- | O₂N-C₆H₃(Me)-Me | HCl | 10 | M: 175–178 |
| 75 | H | —CH=N—N(Bn)- | O₂N-C₆H₃(Me)-Me | — | 10 | M: 175–176; N1: 2.70(3H, s), 5.39 (2H, s), 9.03(1H, s). |

TABLE 9-continued
| | | | | | | |
|---|---|---|---|---|---|---|
| 76 | H | 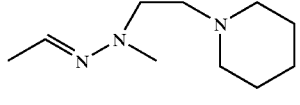 | 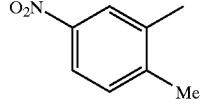 | 2HCl | 13 | M: 228–231; N1: 2.69(3H, s), 8.25 (1H, s), 9.14(1H, s). |
| 77 | H | 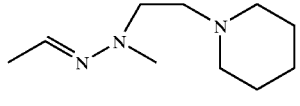 | 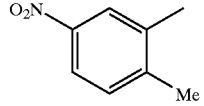 | 2HCl | 13 | M: 215–220(dec); N1: 2.69(3H, s), 8.28 (1H, s), 9.17(1H, s). |
| 78 | H | —CH=N—N(Me)- | 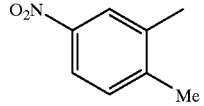 | HCl | 14 | M: 214–217(dec); N1: 3.51(3H, s), 4.04(3H, s), 8.21(1H, s). |
| 79 | H | —CH=N—N(Me)- | 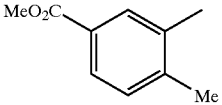 | HCl | 17 | M: 203–206(dec); N1: 2.69 (3H, s),8.28(1H, s), 9.17(1H, s). |
| 80 | H | —CH=N—N(Me)- | 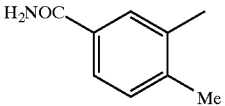 | — | 16 | M: 156–159; N1: 3.46(3H, s), 3.90 (3H, s), 8.21(1H, s). |
| 81 | H | —CH=N—N(Me)- | 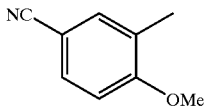 | HCl | 18 | M: 216–218; N1: 3.49(3H, s), 3.98 (3H, s), 8.26(1H, s). |
| 82 | H | —CH=N—N(Me)- | 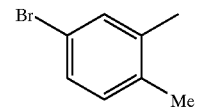 | HCl | 14 | M: 212–215; N1: 3.48(3H, s), 3.88 (3H, s), 7.23(1H, s, J=9.0Hz). |
| 83 | H | —CH=N—N(Me)- | 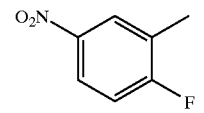 | — | 17 | M: 203–206; N1: 8.03(1H, s), 3.88 (1H, s), 9.34(1H, d, J=1.0Hz). |
| 84 | H | 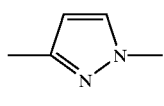 | 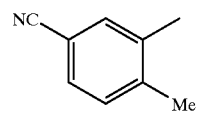 | — | 1 | N1: 7.30(1H, d, J=3.0Hz), 8.35' (1H, s), 8.76(1H, d, J=2.9Hz, 1H), |
| 85 | H | —CH=N—NH— | 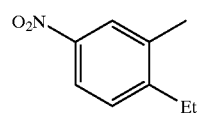 | — | 11 | F: 452 |
| 86 | H | —CH=N—NH— | 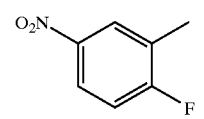 | — | 11 | N1: 8.09(1H, s), 8.35(1H, s), 9.15 (1H, d, J=1.5Hz). |
| 87 | H | —CH=N—NH— | 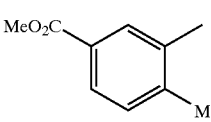 | — | 11 | N1: 3.93(3H, s), 4.08(3H, s), 7.10 (1H, d, J=9.0Hz). |

TABLE 10

[Structure: CH3-CH=N-N(Me)-CH2CH2-piperidine]

| Co | R¹ | R²¹ | R²² | Sal | Syn | Dat |
|---|---|---|---|---|---|---|
| 55 | Br | NO$_2$ | OH | — | 19 | M: 260–262(dec); N1: 3.52(3H, d), 7.41 (1H, d, J=9.0Hz), 9.31(1H, s). |
| 56 | Cl | SO$_2$NH$_2$ | Me | HCl | 20 | N1: 2.65(3H, s), 3.42(3H, s), 7.69(1H, d J=8.0Hz). |
| 57 | F | NO$_2$ | Me | HCl | 21 | M: 226–229; N1: 2.67(3H, s), 3.49(3H, s), 8.33(1H, s). |
| 58 | [AcNH-CH2CH2-NH2] | NO$_2$ | Me | 3HCl | 22 | N1: 2.66(3H, s), 3.52(3H, s), 9.64(1H, s). |
| 59 | Cl | NO$_2$ | NH$_2$ | HCl | 23 | M: 232–234(dec); N1: 3.50(3H, s), 8.37 (1H, d, J=4.0Hz), 9.31(1H, s). |
| 60 | Cl | NO$_2$ | OCH$_2$CF$_3$ | HCl | 24 | M: 216–219; N1: 3.50(3H, s), 8.25(1H, s), 8.32(1H, s). |
| 88 | Cl | NO$_2$ | Me | HCl | 10 | M: 216–217; N1: 2.68(3H, s), 3.50(3H, s), 8.26(1H, s) |
| 89 | Br | CO$_2$H | OMe | — | 15 | M: 262–264(dec); N1: 3.41(3H, s), 3.81 (3H, s), 9.19(1H, s). |
| 90 | Ph | NO$_2$ | Me | HCl | 20 | M: 225–230(dec); N1: 2.68(3H, s), 3.47 (3H, s), 9.77(1H, s). |
| 91 | Br | SO$_2$Me | Me | HCl | 14 | M: 224–228(dec); N1: 2.65(3H, s), 3.28 (3H, s), 3.42(3H, s). |
| 92 | CF$_3$ | NO$_2$ | Me | HCl | 21 | M: 207–209; N1: 2.67(3H, s), 3.48(3H, s), 8.37(1H, s). |
| 93 | CN | NO$_2$ | Me | HCl | 21 | M: 236–238(dec); N1: 2.70(3H, s), 3.47 (3H, s), 9.43(1H, s). |
| 94 | CF$_3$ | CN | Me | HCl | 21 | M: 217–220; N1: 2.63(3H, s), 3.48(3H, s), 9.65(1H, s). |
| 95 | F | CN | Me | HCl | 21 | N1: 2.63(3H, s), 3.46(3H, s), 9.25(1H, s). |
| 96 | CN | CN | Me | HCl | 21 | M: 248–250; N1: 2.68(3H, s), 3.44(3H, s), 9.50(1H, s). |
| 97 | Cl | CN | Me | HCl | 20 | M: 218–220; N1: 2.64(3H, s), 3.51(3H, s), 8.35(1H, s). |
| 98 | Cl | CN | CO$_2$Me | HCl | 20 | M: 245–247(dec); N1: 3.43(3H, s), 3.92 (3H, s), 7.81(1H, dd, J=9.0, 2.0Hz). |
| 99 | Me | NO$_2$ | Me | HCl | 21 | M: 235–238(dec); N1: 2.37(3H, s), 2.69 (3H, s), 3.50(3H, s). |

TABLE 11

| | | | | | | |
|---|---|---|---|---|---|---|
| 100 | CO$_2$Li | NO$_2$ | Me | — | 15 | M: >270; N1: 2.71(3H, s), 3.39(3H, s), 9.30(1H, s). |
| 101 | CO$_2$Et | NO$_2$ | Me | HCl | 21 | N1: 2.71(3H, s), 3.48(3H, s), 10.03(1H, s). |
| 102 | CONH$_2$ | NO$_2$ | Me | HCl | 16 | M: 220–223(dec); N1: 2.68(3H, s), 3.50 (3H, s), 8.42(1H, s). |
| 103 | CONHMe | NO$_2$ | Me | HCl | 16 | N1: 2.64(3H, s), 3.52(3H, s), 9.51(1H, s). |
| 104 | CONMe$_2$ | NO$_2$ | Me | HCl | 16 | N1: 2.65(3H, s), 3.49(3H, s), 9.10(1H, s). |
| 105 | [Ac-morpholine] | NO$_2$ | Me | HCl | 16 | N1: 2.65(3H, s), 3.49(3H, s), 9.08(1H, s). |
| 106 | [Ac-piperazine] | NO$_2$ | Me | 2HCl | 22 | N1: 2.65(3H, s), 3.48(3H, s), 9.08(1H, s). |

TABLE 11-continued
| | | | | | | |
|---|---|---|---|---|---|---|
| 107 | 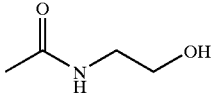 | NO$_2$ | Me | HCl | 16 | N1: 2.65(3H, s), 3.54(3H, s), 9.64(1H, s). |
| 108 | Cl | NO$_2$ | F | HCl | 20 | M: 201–203; N1: 3.45(3H, s), 8.05(1H, s), 8.37(1H, s). |
| 109 | Cl | NO$_2$ | 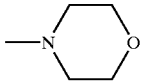 | HCl | 23 | N1: 3.57(3H, s), 8.80(1H, s), 9.03(1H, s). |
| 110 | Cl | NO$_2$ |  | 2HCl | 23 | N1: 3.52(3H, s), 8.27(1H, s), 9.54(1H, s). |
| 111 | Cl | NO$_2$ | NHMe | HCl | 23 | N1: 2.95(3H, d, J=5.0Hz), 3.43(3H, s), 6.96(1H, d, J=10.0Hz). |
| 112 | Cl | NO$_2$ | 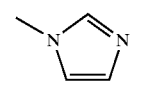 | 2HCl | 23 | M: 214–218(dec); N1: 3.18(3H, s), 7.81 (1H, s), 9.55(1H, s). |
| 113 | Cl | NO$_2$ | NMe$_2$ | HCl | 23 | M: 219–221; N1: 2.93(6H, s), 3.46(3H, s), 7.44(1H, d, J=9.5Hz). |
TABLE 12
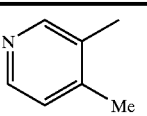
(I)
| Co | R$^1$ | R$^2$ | Sal | Syn | Dat |
|---|---|---|---|---|---|
| 114 | Br | 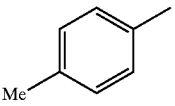 | 2HCl | 20 | M: 224–227(dec); N1: 2.62(3H, s), 3.48(3H, s), 9.09(1H, s). |
| 115 | Br |  | HCl | 20 | N1: 2.37(3H, s), 3.30(3H, s), 8.36(1H, s). |
| 116 | Cl | Me | HCl | 20 | N1: 3.12(3H, s), 3.31(3H, s), 7.97(1H, d, J=9.5Hz). |

TABLE 13
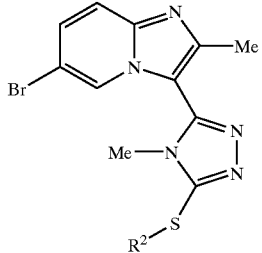
| Co | R² | Sal | Syn | Dat |
|---|---|---|---|---|
| 61 | 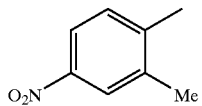 | HCl | 25 | M: 196–198; N1: 2.44(3H, s), 3.46(3H, s), 9.17(1H, s) |
| 62 | 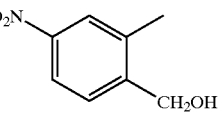 | HCl | 26 | M: 211–213; N1: 3.45(3H, s), 4.70(2H, s), 9.22(1H, s) |
| 63 | 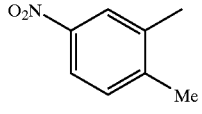 | HCl | 27 | M: 238–240; N1: 2.41(3H, s), 2.60(3H, s), 3.52(3H, s) |
| 117 | 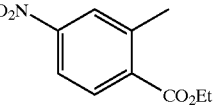 | HCl | 25 | M: 217–219; N1: 3.47(3H, s), 4.28(2H, q, J=6.8 Hz), 9.05(1H, s) |
TABLE 14
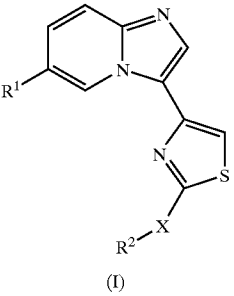
(I)
| Co | R¹ | X | R² | Sal | Syn | Dat |
|---|---|---|---|---|---|---|
| 64 | Br | SO | 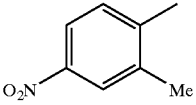 | HCl | 28 | N1: 2.81(3H, s), 8.59(1H, s), 8.68(1H, s) |
| 65 | Cl | SO₂ | 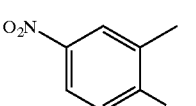 | HCl | 29 | M: 221–223; N1: 2.84(3H, s), 7.64–7.72 (1H, m), 8.50–8.60(2H, m) |

TABLE 14-continued

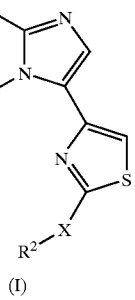

(I)

| Co | R¹ | X | R² | Sal | Syn | Dat |
|---|---|---|---|---|---|---|
| 66 | Cl | S | 2-ethyl-4-nitro-1-methoxyphenyl | — | 30 | N2: 3.99(3H, s), 4.56(2H, s), 7.95(1H, s) |
| 118 | Br | S | 2-methyl-4-nitro-tolyl | HCl | 25 | M: 192–194; N1: 2.57(3H, s), 8.45(1H, s), 8.65(1H, s) |
| 119 | Br | SO₂ | 2-methyl-4-nitro-tolyl | — | 29 | M: 225–228; N1: 2.84(3H, s), 8.28(1H, s), 8.75(1H, s) |
| 120 | Br | S | 2-methyl-4-(trifluoromethyl)tolyl | HCl | 25 | M: 198–201; N1: 7.95(2H, m), 8.66(1H, s), 9.25(1H, s) |
| 121 | Br | SO | 2-methyl-4-(trifluoromethyl)tolyl | HCl | 28 | M: 230–234; N1: 8.64(1H, d, J=7.3Hz), 7.72(1H, d, J=9.7Hz), 9.15(1H, s) |
| 122 | Br | SO | 2-methyl-4-nitro-benzoate ethyl ester | HCl | 28 | M: 210–212(dec); N1: 1.28(3H, t, J=7.3 Hz), 4.39(2H, q, J=7.3Hz), 8.55(1H, s) |
| 123 | Br | SO | 2-methyl-4-nitro-benzoic acid | — | 15 | M: 247–249(dec); N1: 7.67(1H, d, J=9.7 Hz), 8.21(1H, s), 8.45(1H, s) |
| 124 | Cl | S | 2-methyl-4-nitro-benzyl alcohol | HCl | 26 | M: 193–194(dec); N1: 4.78(2H, s), 8.36(1H, s), 8.63(1H, s) |
| 125 | Cl | SO | 2-methyl-4-nitro-benzyl alcohol | HCl | 28 | M: 172–200(dec); N1: 4.88–5.00(2H, m), 7.80–8.00(6H, m), 8.61(1H, s) |

TABLE 14-continued
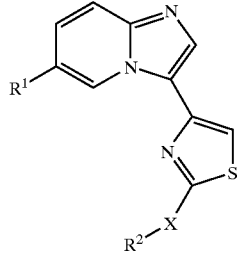
(I)
| Co | R¹ | X | R² | Sal | Syn | Dat |
|----|----|----|----|----|----|----|
| 126 | Cl | SO₂ | 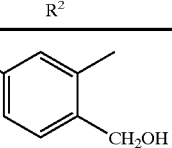 | HCl | 29 | M: 237–239(dec); N1: 5.07(2H, s), 8.18 (1H, d, J=8.7Hz), 8.46(1H, s) |
| 127 | Cl | S | 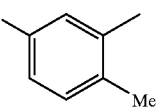 | HCl | 27 | N1: 2.59(3H, s), 7.95(1H, d, J=9.8Hz), 8.64(1H, s) |
| 128 | Cl | SO | 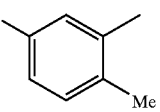 | HCl | 28 | M: 204–206; N1: 2.75(3H, s), 8.57(1H, s), 8.67(1H, s) |
| 129 | Me | S | 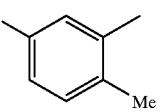 | — | 27 | N1: 7.40(1H, s), 7.87(1H, s), 8.71(1H, s) |
| 130 | Me | SO₂ | 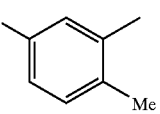 | HCl | 29 | N1: 2.85(3H, s), 7.80(1H, d, J=9.3Hz), 8.70(1H, s) |
| 131 | Cl | S | 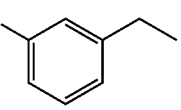 | — | 30 | N2: 4.62(2H, s), 7.39(1H, s), 7.94(1H, s) |
| 132 | Cl | S | 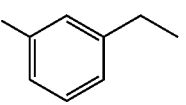 | — | 30 | N2: 4.52(2H, s), 7.39(1H, s), 7.94(1H, s) |

TABLE 15

| Co | T | U | -Y- | Sal | Syn | Dat |
|---|---|---|---|---|---|---|
| 67 | N | N | —CH=N—N(Me)- | HCl | 31 | N1: 3.82(3H, s), 7.56(1H, s), 7.65(1H, d, J=10.0Hz). |
| 68 | N | N | 3-methyl-pyrrolidin-1-yl | HCl | 32 | N1: 2.69(3H, s), 7.49(1H, d, J=10.0Hz), 8.42(1H, d, J=10.0Hz). |
| 69 | CH | CH | 3-methyl-1-methyl-pyrrol-1-yl | HCl | 33 | M: 220–224(dec) N1: 2.70(3H, s), 8.31(1H, s), 8.93(1H, s). |
| 133 | CH | N | —CH=N—N(Me)- | — | 17 | N1: 2.66(3H, s), 3.57(3H, s), 7.80(1H, d, J=9.0 Hz). |
| 134 | N | N | 3-methyl-1-methyl-pyrrol-1-yl | — | 10 | N1: 2.69(3H, s), 7.55(1H, d, J=9.5Hz), 8.54 (1H, s). |
| 135 | CH | CH | MeO$_2$C-4-methyl-1-methyl-pyrrol-1-yl | HCl | 10 | N1: 2.68(3H, s), 3.61(3H, s), 8.81(1H, s). |

TABLE 16

| Co | X | Syn | Dat |
|---|---|---|---|
| 70 | S | 34 | N1: 3.70(3H, s), 4.29(2H, s), 8.25(1H, s) |
| 136 | SO$_2$ | 28 | N2: 3.74(3H, s), 4.35(2H, s), 8.19(1H, d, J=9.6Hz) |

TABLE 17

| Co | R$^1$ | R$^2$ |
|---|---|---|
| 137 | Br | 3-methyl-4-methyl-benzonitrile |
| 138 | Cl | 3-methyl-4-methyl-benzonitrile |
| 139 | CN | 3-methyl-4-methyl-benzonitrile |
| 140 | Br | 3-methyl-4-methyl-nitrobenzene |
| 141 | CN | 3-methyl-4-methyl-nitrobenzene |
| 142 | Ph | 3-methyl-4-methyl-nitrobenzene |
| 143 | Br | 3-methyl-4-amino-benzonitrile |
| 144 | Cl | 3-methyl-4-amino-benzonitrile |
| 145 | CN | 3-methyl-4-amino-benzonitrile |

TABLE 17-continued
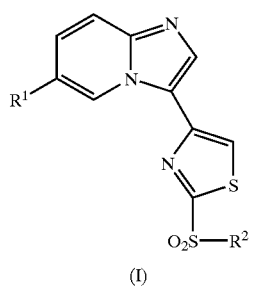
(I)
| Co | R¹ | R² |
|---|---|---|
| 146 | Br | |
| 147 | Cl | |
| 148 | CN | |
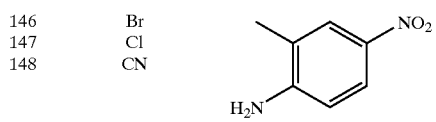
TABLE 18
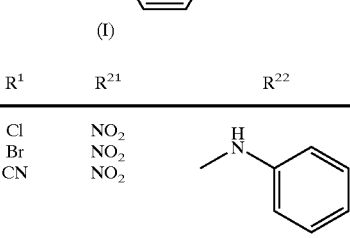
(I)
| Co | R¹ | R²¹ | R²² |
|---|---|---|---|
| 149 | Cl | CN | |
| 150 | Br | CN | |
| 151 | CN | CN | |
| 152 | Cl | CN | |
| 153 | Br | CN | |
| 154 | CN | CN | |
| 155 | Cl | NO₂ | |
| 156 | Br | NO₂ | |
| 157 | CN | NO₂ | |
| 158 | Cl | NO₂ | |
| 159 | Br | NO₂ | |
| 160 | CN | NO₂ | |
| 161 | Cl | CN | |
| 162 | Br | CN | |
| 163 | CN | CN | |
| 164 | Cl | CN | |
| 165 | Br | CN | |
| 166 | CN | CN | |
TABLE 18-continued
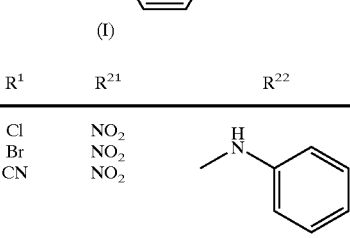
(I)
| Co | R¹ | R²¹ | R²² |
|---|---|---|---|
| 167 | Cl | NO₂ | |
| 168 | Br | NO₂ | |
| 169 | CN | NO₂ | |
| 170 | Cl | NO₂ | |
| 171 | Br | NO₂ | |
| 172 | CN | NO₂ | |
| 173 | Cl | CN | |
| 174 | Br | CN | |
| 175 | CN | CN | |
| 176 | Cl | CN | |
| 177 | Br | CN | |
| 178 | CN | CN | |
| 179 | Cl | NO₂ | |
| 180 | Br | NO₂ | |
| 181 | CN | NO₂ | |
| 182 | Cl | NO₂ | |
| 183 | Br | NO₂ | |
| 184 | CN | NO₂ | |
TABLE 19
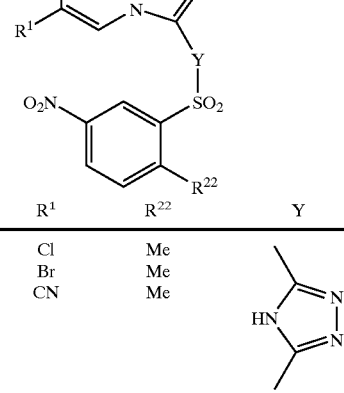
| Co | R¹ | R²² | Y |
|---|---|---|---|
| 185 | Cl | Me | |
| 186 | Br | Me | |
| 187 | CN | Me | |

TABLE 19-continued

| Co | R¹ | R²² | Y |
|---|---|---|---|
| 188 | Cl | Me | |
| 189 | Br | Me | 2,4-dimethyl-1H-imidazol-5-yl |
| 190 | CN | Me | |
| 191 | Cl | Me | |
| 192 | Br | Me | 2,5-dimethylthiophen-3-yl |
| 193 | CN | Me | |
| 194 | Cl | Me | |
| 195 | Br | Me | 2,5-dimethyloxazol-4-yl |
| 196 | CN | Me | |
| 197 | Cl | NH₂ | |
| 198 | Br | NH₂ | 3,5-dimethyl-1H-1,2,4-triazol-yl |
| 199 | CN | NH₂ | |
| 200 | Cl | NH₂ | |
| 201 | Br | NH₂ | 2,4-dimethyl-1H-imidazol-5-yl |
| 202 | CN | NH₂ | |
| 203 | Cl | NH₂ | |
| 204 | Br | NH₂ | 2,5-dimethylthiophen-3-yl |
| 205 | CN | NH₂ | |
| 206 | Cl | Me | |
| 207 | Br | Me | 2,5-dimethyloxazol-4-yl |
| 208 | CN | Me | |

TABLE 19-continued

| Co | R¹ | R²² | Y |
|---|---|---|---|
| 209 | Cl | Me | |
| 210 | Br | Me | 2,5-dimethyloxazol-4-yl |
| 211 | CN | Me | |
| 212 | Cl | Me | |
| 213 | Br | Me | 2,5-dimethylfuran-3-yl |
| 214 | CN | Me | |
| 215 | Cl | Me | |
| 216 | Br | Me | 2,5-dimethyl-1,3,4-thiadiazol-yl |
| 217 | CN | Me | |
| 218 | Cl | NH₂ | |
| 219 | Br | NH₂ | 2,5-dimethyloxazol-4-yl |
| 220 | CN | NH₂ | |
| 221 | Cl | NH₂ | |
| 222 | Br | NH₂ | 2,5-dimethyloxazol-4-yl |
| 223 | CN | NH₂ | |
| 224 | Cl | NH₂ | |
| 225 | Br | NH₂ | 2,5-dimethylfuran-3-yl |
| 226 | CN | NH₂ | |
| 227 | Cl | Me | |
| 228 | Br | Me | 3,5-dimethyl-1,2,4-thiadiazol-yl |
| 229 | CN | Me | |

TABLE 19-continued

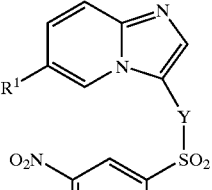

| Co | R¹ | R²² | Y |
|---|---|---|---|
| 230 | Cl | Me | 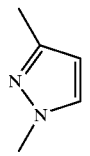 |
| 231 | Br | Me | |
| 232 | CN | Me | |
| 233 | Cl | Me | 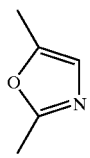 |
| 234 | Br | Me | |
| 235 | CN | Me | |
| 236 | Cl | NH₂ | 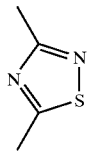 |
| 237 | Br | NH₂ | |
| 238 | CN | NH₂ | |
| 239 | Cl | NH₂ | 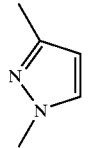 |
| 240 | Br | NH₂ | |
| 241 | CN | NH₂ | |
| 242 | Cl | NH₂ | 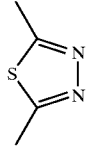 |
| 243 | Br | NH₂ | |
| 244 | CN | NH₂ | |
| 245 | Cl | NH₂ | |
| 246 | Br | NH₂ | |
| 247 | CN | NH₂ | |

EXAMPLES

The present invention will be described in more detail by referring to the following EXAMPLES but is not deemed to be limited thereto.

The following Tables 1~3 show starting compounds which were used in EXAMPLES, and Tables 4~19 show structural formulas as well as physicochemnical properties of the compounds of the present invention. Moreover, the compounds of the present invention with structural formulas shown in Tables 17–19 can be easily produced in the same manner as in the EXAMPLES mentioned hereinafter or in accordance with the Production Methods mentioned hereinabove, or by applying thereto some modifications which are obvious to those skilled in the art.

In the tables, abbreviations are used to mean the following.

Rco: starting compounds number
Co: compounds number of the present invention
Str: structural formula
Sal: salt
Syn: production method (a following number represents a number of an EXAMPLE described hereinbelow, indicating that the compound was produced using the method described in the EXAMPLE or a similar method.)
Dat: physicochemical properties wherein:
  F: FAB-MS (M+H)⁺
  FN: FAB-MS (M−H)⁻
  E: EI-MS
  M: melting point [° C.]
  N1: characteristic peaks δ ppm of NMR (DMSO-d₆, TMS internal standard)
  N2: characteristic peaks δ ppm of NMR (CDCl₃, TMS internal standard)
  HPLC: retention time [min] of compound in HPLC assay
  <HPLC conditions:
    column: Wakosil-II 5C18AR, 4.6×30 mm
    detection wavelength: 254 nm
    column temperature: 35° C.
    flow rate: 1.0 ml/min
    eluent: 5 mM TFA methanol solution/5 mM TFA aqueous solution=5/95<0 min>−100/0<30 mins: linear gradient>−100/0<35 mins>>;
Ph: phenyl
Naph: 2-naphthyl
Ac: acetyl
Bn: benzyl
3,5—CF₃—Ph: 3,5-bis(trifluoro) phenyl
Boc: t-butoxycarbonyl
Bz: benzoyl
iPr: isopropyl
A number preceding a substituent represents a substitution position. For example, "4-OMe" means that a methoxy group is substituted at 4-position.

Production methods of the starting compounds shown in said Tables 1~3 are explained hereinbelow.

Compound a1: 3-Chloroacetylacetone was added to an ethanol solution of 2-amino-5-bromopyridine and the solution was refluxed for 17 hours. The reaction solution was concentrated. The obtained residue was purified with column chromatography to give Compound a1.

Compound b1: Compound a1, phenylboronic acid, sodium carbonate, and tetrakis(triphenylphosphine) palladium in a mixture of water and dimethoxyethane were refluxed for 5 hours. After the solution was allowed to cool, water and brine were added and extracted with chloroform. The combined organic layer was concentrated under reduced pressure. The residue was purified with silica gel column chromatography to give Compound b1.

Compound c1: N,N-Dimethylfornamide dimethylacetal was added to Compound a1 and the mixture was heating with stirring at an oil bath temperature of 130° C. for 2 days. After the solution was allowed to cool, insoluble materials were filtered off and the filtrate was concentrated under reduced pressure. Hydrazine monohydrate and ethanol were added to the obtained residue and the mixture was refluxed for 1.5 hours. After the mixture was allowed to cool, precipitated crystals were filtered to give Compound c1.

Compound d1: 3-Chloroacetylacetone was added to a solution of 2-amino-5-methylpyridine in ethanol and the solution was refluxed. The reaction solution was concentrated and N,N-dimethylformamide dimethylacetal was added to the obtained residue and the mixture was heated with stirring. After the mixture was allowed to cool, insoluble materials were filtered off and the filtrate was concentrated under reduced pressure. Hydrazine monohydrate and ethanol were added to the obtained residue and the mixture was refluxed. After the mixture was allowed to cool, precipitated crystals were filtered to give Compound d1.

Compound e1: A solution of 6-bromoimidazo[1,2-a]pyridine in DMF was added in dropwise to a solution of phosphorus oxychloride in DMF. The reaction mixture was stirred at a bath temperature of 125° C. for 0.5 hours, then at 80° C. for 3 hours and then at 100° C. for 3 hours. The reaction mixture was poured into crushed ice and was then neutralized with sodium hydroxide. The solution was extracted with ethyl acetate and a small amount of THF. The organic layer was concentrated under reduced pressure. The obtained solid was washed with chloroform to give Compound e1.

Compound f1: Acetyl chloride was dropped into a mixture of 6-bromoimidazo[1,2-a]pyridine and aluminum chloride (III) under an argon atmosphere with ice cooling. The mixture was stirred at 4° C. for 4 hours. After this reaction solution was diluted with chloroform, water was slowly added. After the solution was basified, the solution was filtered through Celite and the filtrate was extracted with ethyl acetate. The solvent was evaporated. The obtained residue was purified with silica gel column chromatography to give Compound f1.

Compound g1: Bromine was added in dropwise to a suspension of Compound f1 in 25% hydrogen bromide/acetic acid at room temperature. After the solution was stirred at room temperature for 12 hours, insoluble materials were filtered to give Compound g1.

Compound h1: A mixture of Compound a1, ethanol and hydrazine monohydrate was heated under reflux for 2 days. The reaction mixture was concentrated under reduced pressure, diluted with chloroform and washed with water. The organic layer was dried over anhydrous magnesium sulfate and concentrated under reduced pressure. The obtained residue was purified with silica gel column chromatography to give Compound h1.

Compound i1: Benzoyl isothiocyanate was added in dropwise to a solution of N-isopropyl-2-methyl-5-nitroaniline in chloroform under ice cooling. After the reaction solution was stirred at room temperature for 20 hours, the solution was concentrated under reduced pressure. The residue was dissolved in 40% methylamine/methanol and the solution was stirred in a sealed tube at 100° C. for 24 hours. The reaction mixture was concentrated. The residue was purified with silica gel column chromatography to give Compound i1.

Compound j1: Benzoyl isothiocyanate was added in dropwise to a solution of 6-nitro-2,3-dihydro-1H-indolein chloroform under ice cooling. After the reaction solution was stirred at room temperature for 2 hours, insoluble materials were filtered. 40% Methylamine/methanol was added to the obtained solids and the mixture was stirred at room temperature for 3 hours and then at 50° C. for 19 hours. The reaction mixture was cooled to room temperature. Insoluble solids were filtered to give Compound j1.

Compound k1: Methyl 4-methyl-benzoate was added to chldrosulfonic acid under ice cooling and stirred for 5 hours After pouring the reaction solution into water and ice, precipitates were filtered to give Compound k1.

Compound m1: Methyl 4-cyano-2-methylbenzoate was added to concentrated sulfuric acid. Aqueous sodium nitrite was added at −10° C. and the reaction mixture was stirred for 30 minutes. Under ice cooling, the reaction mixture was added to acetic acid which was saturated with sulfur dioxide gas in the presence of cupric chloride, and then stirred at room temperature for 18 hours. After the reaction mixture was concentrated under reduced pressure to an approximately one-third volume, water was added and the obtained precipitates were collected to give Compound m1.

Compound n1: 3-Chloro-6-hydrazinopyrazine and EDCI hydrochloride were added to a solution of pyrrole-3-carboxylic acid in methylene chloride and was stirred for 20 hours. The reaction mixture was concentrated under reduced pressure and washed with water to give Compound n1.

Compound p1: A solution of Compound n1 in acetic acid was stirred at 100° C. for 4 hours. The reaction mixture was concentrated under reduced pressure and washed with water to give Compound p1.

Compound q1: A solution of Compound n3 in acetic acid was refluxed for 2 days. The reaction mixture was concentrated under reduced pressure, the residue was dissolved in ethanol. 4M Hydrogen chloride/ethyl acetate was added to the solution and the obtained precipitates were collected. The obtained solid was dissolved in methanol and ozone gas was introduced to the solution at −78° C. for 1 hour. Then, dimethyl sulfide was added and the reaction mixture was stirred at room temperature for 10 hours. The reaction mixture was concentrated and purified with silica gel column chromatography to give Compound q1.

Compound r1: A solution of Compound n5 in acetic acid was heated at 100° C. for 18 hours. After the reaction mixture was concentrated under reduced pressure and diluted with ethyl acetate, water and ethyl acetate were added. The separated organic layer was dried over anhydrous sodium sulfate and concentrated under reduced pressure. The residue was recrystallized from ethanol and then dissolved in methanol. After ozone gas was introduced to the reaction solution at −78° C. for 1 hour, dimethyl sulfide was added, followed by stirring at room temperature for 1 hour. The resulting precipitate was collected to give Compound r1.

Compound s1: Methyl diethylphosphonoacetate and potassium carbonate were added subsequently to a solution of 6-chloroimidazo[1,2-a]pyrizin-3-carboaldehyde in DMF, and stirred at 90° C. for 4 hours. Then, the reaction solution was poured into water and the precipitated solid was collected to give Compound s1.

Compound t1: A solution of Compound s1 in DMSO-diethyl ether and tosylmehylisocyanide was slowly added to a suspension of 60% sodium hydride in diethyl ether at room temperature. After the reaction solution was stirred for 1 hour, it was concentrated under reduced pressure and the residue was washed with water and ether to give Compound t1.

Compound u1: Sodium borohydride was added to a suspension of Compound g2 in methanol and the reaction mixture was stirred at room temperature for 2 hours. The solvent was evaporated, and ethyl acetate and water were added to the residue. The separated organic layer was concentrated and the residue was crystallized from ether and chloroform. 40% Methylamine/methanol was added to this and stirred at room temperature for 4 hours. After concentration, the residue was dissolved with chloroform and a small amount of methanol. After washing with saturated aqueous sodium hydrogencarbonate, the organic layer was concentrated. The obtained residue was purified with silica gel column chromatography to give Compound u1.

Compound v1: Ethanol and hydrazine monohydrate were added to ethyl 6-bromo-2-methylimidazo[1,2-a]pyridin-3-carboxylate and stirred at room temperature for 19 hours. The reaction mixture was concentrated and water was added to the residue. The resulting solid was collected to give Compound v1.

Compound w1: Tosylmethylisocyanide was added in portionwise to a suspension of potassium t-butoxide in THF at −70° C. After stirring for 30 minutes, 6-chloroimidazo[1,2-a]pyridin-3-carboaldehyde was added in one portion at −60° C. After stirring under dry ice-acetonitrile for 0.5 hour, methanol was added and the resulting mixture was refluxed for 1 hour. After concentration, the reaction mixture was neutralized with acetic acid, the resulting mixture was extracted with chloroform. The organic layer was dried over anhydrous magnesium sulfate, and purified with silica gel column chromatography to give Compound w1.

Compound x1: Methyl isothiocyanate was added to a suspension of Compound v1 in THF and chloroform. After stirring at 70° C. for 2 hours, the reaction mixture was concentrated. The residue in 2M sodium hydroxide was refluxed for 3 hours. After cooling to room temperature, it was neutralized with 12M hydrochloric acid and the precipitated solids were filtered to give Compound x1.

Compound y1: Ammonium dithiocarbamate was added to a suspension of Compound g1 in methanol and the reaction mixture was stirred at room temperature for 15 minutes. The collected solid was refluxed in acetic acid for 2.5 hours. After cooling to room temperature, the solids were washed with hot methanol and collected to give Compound y1.

Among the starting compounds shown in Tables 1~3, Compounds a2~a6 were obtained using a similar method as that in Compound a1, Compounds c2~c8 were obtained using a similar method as that in Compound c1, Compounds g2~g4 were obtained using a similar method as that in Compound g1, Compound j2 was obtained using a similar method as that in Compound j1, Compounds m2~m4 were obtained using a similar method as that in Compound m1, Compounds n2~n5 were obtained using a similar method as that in Compound n1, Compound p2 was obtained using a similar method as that in Compound p1, Compounds y2~y3 were obtained, using a similar method as that in Compound y1, and Compound b2 was obtained using a similar method as that in Compound b1.

Example 1

Benzenesulfonyl chim ride was added to a mixture of Compound (0.10 g) and pyridine (2.5 ml) an d the resulting mixture was stirred at 100° C. for 4 hours. After concentration, the residue was diluted with ethyl acetate, washed with saturated aqueous sodium hydrogencarbonate, dried over anhydrous magnesiumn sulfate, and concentrated under reduced pressure. The obtained residue was purified with silica gel column chromatography (eluent:chloroform:methanol=100:0–99:1) to give Compound 1(0.11 g).

Example 2

Thionyl chloride (5 ml) was added to 2-methyl-5-nitrobenzoic acid (500 mg). The re action mixture was refluxed for one hour and then concentrated under reduced pressure, and dried in vacuo. THF (10 ml), chloroform (10 ml), TEA (2 g) and Compound c1 (440 mg) were added to the obtained solids. The mixture was stirred at room temperature for 3 hours, diluted with chloroform and washed with water and saturated aqueous sodium hydrogencarbonate. The obtained organic layer was dried over anhydrous magnesium sulfate and concentrated under reduced pressure. The obtained solids were purified with silica gel column chromatography (eluent:chloroform:methanol=200:1) to give Compound 31 (72 mg).

Example 3

Pyridine (10 ml) and 5-nitro-2-methylbenzenesulfonylchloride (1.1 g) were added to Compound h1 (1.2 g), and the mixture was stirred for 5 hours. The reaction mixture was concentrated under reduced pressure and the residue was diluted with chloroform and washed with water. The organic layer was dried over anhydrous magnesium sulfate and concentrated under reduced pressure. The obtained residue was crystallized from chloroform, and washed with hot methanol to give Compound 32 (1.47 g).

Example 4

A mixture of (2-methyl-5-nitrophenyl)thiourea (350 mg), Compound g2 (430 mg) and ethanol (10 ml) was refluxed for 2 hours. After the mixture was allowed to cool, ethanol (5 ml) was added and insoluble materials were collected. The obtained solids were recrystallized from methanol to give Compound 33 (181 mg). In a similar manner, Compounds 39, 40 and 45 were obtained.

Example 5

A mixture of Compound f1 (2.01 g), hydrazine monohydrate (5.0 g) and ethanol (20 ml) was refluxed for 15 hours. The reaction mixture was concentrated. After dilution with ethyl acetate, the mixture was washed with brine. The organic layer was dried over anhydrous magnesium sulfate and concentrated under reduced pressure to give solids of 1-(6-bromoimidazo[1,2-a]pyridin-3-yl)ethylidenehydrazine. Pyridine (20 ml) and 5-nitro-2-methylbenzenesulfonylchloride (2.4 g) were added to the obtained solids at room temperature. The mixture was stirred for 1 hour, and concentrated under reduced pressure. The residue was diluted with ethyl acetate and washed with water and brine. The resulting organic layer was dried over anhydrous magnesium sulfate and concentrated under reduced pressure. The obtained solids were purified with silica gel column chromatography (eluent:chloroform:methanol=100:1) to give 1.06 g of solids. Then, 320 mg of the solids were washed with hot ethanol to give Compound 34 (205 mg). In a similar manner, Compound 41 was obtained.

Example 6

A mixture of Compound i1 (390 mg), Compound g1 (590 mg), ethanol (5 ml) and methanol (3 ml) was refluxed for 24 hours. The reaction mixture was concentrated. Ethanol was added to the obtained foamy residue and resulting insoluble materials were filtered off and the filtrate was concentrated. The residue was crystallized from ethanol and ethyl acetate and then recrystallized from ethanol and ether. In order to remove impurities with high crystallinity, the obtained solids were dissolved in methanol (50 ml) and sodium borohydride (100 mg) was added to the solution at room temperature. The reaction mixture was stirred for 15 minutes and concentrated under reduced pressure. The residue was diluted with ethyl acetate and washed with saturated aqueous sodium hydrogencarbonate and brine. After the solution was dried over anhydrous magnesium sulfate, the solution was concentrated under reduced pressure. The residue was purified with silica gel column chromatography (eluent:chloroform:methanol=100:1). The combined eluent which contained target compound was collected and 4M hydrochloric acid/ethyl acetate (0.3 ml) was added to the solution, which was concentrated under reduced pressure. The obtained residue was crystallized from ethanol-ether to give Compound 35 (146 mg).

Example 7

Compound 32 (500 mg) and methyl iodide (198 mg) were added subsequently to a suspension of 60% sodium hydride (50 mg) in DMF (10 ml). After stirring at room temperature for 10 minutes, the reaction mixture was diluted with ethyl acetate and washed with water and brine. The organic layer was dried over anhydrous magnesium sulfate and concentrated under reduced pressure. The residue was purified with silica gel column chromatography (eluent:chloroform). The obtained solids were washed with hot methanol to give Compound 36 (230 mg). In a similar manner, Compounds 42~44 were obtained.

Example 8

3-Bromomethylbenzonitrile (543 mg) and potassium carbonate (383 mg) were added to a solution of Compound c1 (698 mg) in DMF (10 ml) and the mixture was stirred at room temperature for 1.5 hours. Then, 3-bromomethylbenzonitrile (270 mg) and potassium carbonate (200 mg) were added and the mixture was stirred at room temperature for 1 hour. The solvent was evaporated. The resulting residue was diluted with ethyl acetate, washed with water and extracted from ethyl acetate. The combined organic layer was washed with brine and dried over anhydrous magnesium sulfate and concentrated. The obtained residue was purified with silica gel column chromatography (eluent:chloroform:methanol=99:1). Recrystallization (ethanol) gave Compound 37 (439 mg).

Example 9

3—Nitrophenyl acetate (375 mg), 1-hydroxybenzotriazole (280 mg) and EDCI hydrochloride (397 mg) were added to a solution of Compound c1 (698 mg) in DMF (20ml) and the mixture was stirred at room temperature for 16 hours. Water was added to this reaction mixture and solid was collected and washed with water and diethyl ether. The obtained solid was recrystallized from chloroform to give Compound 38 as a 0.2 hydrate (93 mg).

Example 10

Compound 41 (1.5 g) was added to a suspension of 60% sodium hydride (165 mg) in DMF (30 ml) and the reaction mixture was stirred at room temperature for 1 hour. Methyl iodide (540 mg) was added to it and the resulting mixture was stirred at room temperature for 2 hours. Water and ethyl acetate were added to the reaction mixture, and the separated organic layer was washed with brine and dried over anhydrous magnesium sulfate. After the solvent was evaporated, the residue was purified with silica gel column chromatography (eluent:chloroform:methanol=50:1). 4M Hydrogen chloride/ethyl acetate (0.9 ml) was added to the combined eluent which contained the target compound, and the mixture was concentrated under reduced pressure. The obtained solids was recrystallized from methanol to give Compound 46 (982 mg).

Example 11

2-Methyl-5-nitrobenzenesulfonyl chloride (950 mg) was added to a solution of Compound u1 in pyridine (10 ml). The reaction mixture was stirred at room temperature overnight and concentrated. It was diluted with ethyl acetate and washed with saturated aqueous sodium hydrogencarbonate and brine. The organic layer was dried over anhydrous sodium sulfate and concentrated. The residue was purified with silica gel column chromatography (eluent:chloroform:methanol=100:1). Out of the obtained foamy material 450 mg, 250 mg was crystallized from chloroform and ether to give Compound 47 (146 mg).

Example 12

A suspension of Raney nickel in ethanol (20 ml) and concentrated aqueous ammonia (5 ml) were added to a solution of Compound w1 (450 mg) in methanol (20 ml) and THF (20 ml) and the mixture was stirred in hydrogen atmosphere at 1 atm for 9 hours. After unsoluble materials were filtered, the filtrate was concentrated. The obtained residue was dissolved in pyridine (20 ml), 2-methyl-5-nitrobenzenesulfonyl chloride (400 mg) was added to it, and the reaction mixture was stirred at room temperature overnight and concentrated. Chloroform and saturated aqueous sodium hydrogencarbonate were added and the separated organic layer was dried over anhydrous sodium sulfate and concentrated. The residue was purified with silica gel column chromatography (eluent:chloroform:methanol=50:1). The obtained residue was dissolved in THF and methanol, 4M hydrogen chloride/ethyl acetate (0.2 ml) was added to it, and the solution was concentrated under reduced pressure. The residue was recrystallized from methanol to give Compound 48 (156 mg).

Example 13

Cesium carbonate (400 mg) and allyl bromide (110 mg) were added to a solution of Compound 41 (200 mg) in DMF (2 ml) and the reaction mixture was stirred for 3 hours. The concentrated reaction mixture was purified with silica gel column chromatography (eluent:chloroform:methanol=20:1). 4M Hydrogen chloride/ethyl acetate (1.0 ml) was added to the combined eluent which contained the target compound, and the resulting solution was concentrated under reduced pressure. The obtained residue was washed with ethanol to give Compound 49 (150 mg).

Example 14

Hydrazine monohydrate (3.5 ml) was added to a solution of Compound e1 (1.0 g) in ethanol (20 ml) and the mixture was refluxed for 1 hour. The reaction mixture was concentrated under reduced pressure, the obtained residue was dissolved in pyridine (15 ml), methyl 3-chlorosulfonyl-4-methylbenzoate (1.2 g) was added to it and the reaction solution stirred for 3 hours. After the concentrated reaction mixture was purified with silica gel column chromatography (eluent:chloroform:methanol=20:1), it was dissolved in DMF. Potassium carbonate (140 mg) and methyl iodide (100 mg) were added and the reaction mixture was stirred for 18 hours. The reaction solution was purified with silica gel column chromatography (eluent:chloroform:methanol= 20:1). 4M Hydrogen chloride/ethyl acetate (1.0 ml) was added to the combined eluent which contained the target compound, and the solution was concentrated under reduced pressure. The obtained residue was recrystallized from ethanol to give Compound 50 (98 mg).

Example 15

Methanol (30 ml) and 10M aqueous sodium hydroxide (4.0 ml) were added to Compound 50 (1.1 g), and the mixture was stirred for 18 hours. The precipitated solid was collected and washed with ethanol to give Compound 51 (260 mg).

Example 16

Methanol (10 ml) and 4M hydrogen chloride/ethyl acetate (5.0 ml) were added to Compound 51 (700 mg), and the obtained precipitates were filtered. THF (5.0 ml) and CDI (330 mg) were added to this. The reaction mixture was stirred at 70° C. for 1 hour, and then concentrated aqueous ammonia (1.0 ml) was added at room temperature. The resulting mixture was concentrated, washed with water, and dissolved in methanol (10 ml). 4M Hydrogen chloride/ethyl acetate (1.0 ml) was added to the solution and the resulting solution was concentrated under reduced pressure. The obtained residue was washed with ethanol to give Compound 52 (190 mg).

Example 17

Potassium carbonate (410 mg) and methyl iodide (230 mg) were added to a solution of Compound 85 (670 mg) in DMF (3.0 ml) and the mixture was stirred for 2 hours. The resulting mixture was poured into water, and the obtained precipitates were collected and dissolved in methanol (10 ml). 4M Hydrogen chloride/ethyl acetate (1.0 ml) was added to it, and the reaction solution was concentrated under reduced pressure. The obtained residue was washed with ethanol to give Compound 53 (64 mg).

Example 18

Phosphorus oxychloride (5.0 ml) was added to a free form of Compound 52 (300 mg) and the mixture was stirred at 60° C. for 2 hours. After the reaction mixture was concentrated, 4M hydrogen chloride/ethyl acetate (1.0 ml) was added and the solution was concentrated under reduced pressure. The obtained residue was recrystallized from ethanol to give Compound 54 (118 mg).

Example 19

Trimethylsiloxy potassium (130 mg) was added to a solution of Compound 83 (300 mg) in THF (10 ml) and the mixture was stirred for 12 hours. 4M Hydrogen chloride/ ethyl acetate (1.0 ml) was added to the reaction solution and the reaction solution was concentrated under reduced pressure. The obtained residue was washed with methanol and water to give Compound 55 (250 mg).

Example 20

Methylhydrazine (80 mg) was added to a solution of 6-chloroimidazo[1,2-a]pyridine-3-carboaldehyde (400 mg) in ethanol (5.0 ml) and the mixture heated at 60° C. for 2 hours. The reaction solution was concentrated under reduced pressure, the obtained residue was dissolved in pyridine (5.0 ml), 2-methyl-5-sulfamoylbenzenesulfonyl chloride (590 mg) was added and the reaction solution was stirred for 2 hours. The reaction solution was concentrated under reduced pressure. 4M Hydrogen chloride/ethyl acetate (1.0 ml) was added to the obtained residue. Then, the reaction solution was concentrated under reduced pressure, and washed with ethanol to give Compound 56 (740 mg).

Example 21

2-Bromomalonoaldehyd (1.4 g) was added to a solution of 2-amino-5-fluoropyridine (500 mg) in ethanol (5.0 ml) and the mixture was refluxed for 2 hours. The reaction mixture was concentrated under reduced pressure, and the obtained residue was washed with ethyl acetate. Then, ethanol (10 ml) and methylhydrazine (140 mg) were added, and the resulting mixture was heated at 60° C. for 2 hours and concentrated under reduced pressure. The obtained residue was dissolved in pyridine (5.0 ml). 2-Methyl-5-nitrobenzenesulfonyl chloride (800 mg) was added to the solution. The resulting mixture was stirred for 12 hours and concentrated under reduced pressure, and 4M hydrogen chloride/ethyl acetate (1.0 ml) was added to the obtained residue. Then, the mixture was concentrated under reduced pressure, and washed with ethanol to give Compound 57 (150 mg).

Example 22

Methanol (10 ml) and 4M hydrogen chloride/ethyl acetate (1.0 ml) were added to Compound 100 (220 mg) and the obtained precipitates were collected. THF (5.0 ml) and CDI (330 mg) were added to this and the mixture was stirred for 3 hours. Then, t-butyl 2-aminoethylcarbamate (160 mg) was added at room temperature. After the reaction mixture was concentrated, it was dissolved in methanol (2.0 ml). 4M Hydrogen chloride/ethyl acetate (2.0 ml) was added to it and stirred for 0.5 hour. The precipitates were collected and washed with methanol and ether to give Compound 58 (230 mg).

Example 23

Concentrated aqueous ammonia (1.0 ml) was added to a solution of a free form of Compound 108 (150 mg) in THF (5.0 ml), and the mixture was stirred at 60° C. for 7 hours. Then, the reaction mixture was concentrated under reduced pressure. The obtained residue was washed with water and dissolved in methanol (2.0 ml). 4M Hydrogen chloride/ethyl acetate (1.0 ml) was added to it and the solution was concentrated under reduced pressure. The obtained residue was washed with methanol to give Compound 59 (69 mg).

Example 24

2,2,2-Trifluoroethanol (50 mg) and 60% sodium hydride (20 mg) were added to a solution of Compound 108 (130 mg) in THF (5.0 ml) and the mixture was stirred for 2 hours. Then, the reaction mixture was concentrated under reduced pressure. After the obtained residue was washed with water, it was dissolved in methanol (2.0 ml) and 4M hydrogen chloride/ethyl acetate (1.0 ml) was added to it. The solution was concentrated under reduced pressure and the obtained residue was washed with methanol to give Compound 60 (61 mg).

Example 25

Compound x1 (808 mg) and 2-fluoro-5-nitrotoluene (430 mg) were added to a suspension of 60% sodium hydride (110 mg) in DMF (20 ml). After stirring at 70° C. for 6 hours, 2-fluoro-5-nitrotoluene (400 mg) was added and the mixture was stirred at 90° C. for 18 hours. The reaction mixture was concentrated and saturated aqueous sodium hydrogencarbonate and ethyl acetate were added to the residue. The organic layer was separated, washed with saturated aqueous sodium hydrogencarbonate and brine, dried over anhydrous sodium sulfate and concentrated. The residue was purified with silica gel column chromatography (eluent:chloroform). Out of the obtained residue 730 mg, 215 mg was dissolved in chloroform and methanol. 4M Hydrogen chloride/ethyl acetate (0.125 ml) was added to it, and the solution was concentrated under reduced pressure. The residue was recrystallized from ethanol and washed with methanol-ethanol to give Compound 61 (143 mg).

Example 26

Ethanol (20 ml), THF (10 ml), methanol (10 ml) and 1M aqueous sodium hydroxide (2.0 ml) were added to a free form of Compound 117 (561 mg) and the mixture was refluxed for 30 minutes. The reaction mixture was neutralized with 1M hydrochloric acid (2.0 ml) and concentrated. After the obtained crystals were collected, the filtrate was concentrated to a residue and the residue was purified with silica gel column chromatography (eluent:chloroform:methanol=10:1). This was combined with the previously collected crystals, and THF (10 ml) and a 1M borane/THF solution (2 ml) were added to it. The reaction mixture was refluxed for 1 hour. After being allowed to cool, the reaction was quenched with methanol and water under ice bath cooling. The reaction solution was concentrated. Methanol (50 ml) and 1M hydrochloric acid (20 ml) were added to the obtained residue and the mixture was heated at 80° C. After being allowed to cool, the solvent was evaporated and the residue was dissolved in methanol and chloroform. 4M Hydrogen chloride/ethyl acetate (75 μl) was added to it, and the solution was concentrated. The obtained residue was recrystallized from ethanol to give Compound 62 (100 mg).

Example 27

An aqueous solution (5 ml) of sodium nitrile (930 mg) was added in dropwise to a suspension of 2-methyl-5-nitroaniline (2 g) in 6M hydrochloric acid at below 0° C. After stirring at the same temperature for 30 minutes, an aqueous solution (10 ml) of sodium tetrafluoroborate (2 g) was added to it. After stirring with ice bath cooling for 30 minutes, the obtained diazonium salts were collected. Compound x1 (1.5 g) and the collected diazonium salts were added to a suspension (30 ml) of 60% sodium hydride (192 mg) in DMSO, followed by stirring for 15 minutes. As the reaction mixture became more viscous, additional DMSO (20 ml) was added to it. After stirring for 30 minutes, ethyl acetate, water and saturated aqueous sodium hydrogencarbonate were added to it. The obtained crystals were collected and purified with silica gel column chromatography (eluent:chloroform→chloroform:methanol=10:1). The obtained solids were dissolved in chlorofirm and methanol. 4M Hydrogen chloride/ethyl acetate (0.25 ml) was added to the solution, and it was concentrated. The obtained solids were recrystallized from methanol to give Compound 63 (180 mg).

Example 28

Oxone (Brand name: manufactured by Aldrich) (300 mg) was added to a suspension of a free form of Compound 118 (200 mg) in methanol (20 ml). After stirring at room temperature for 18 hours, saturated aqueous sodium hydrogencarbonate was added to it. After extraction with ethyl acetate, the organic layer was dried over anhydrous magnesium sulfate, concentrated and purified with silica gel column chromatography (eluent:chloroform→chloroform:methanol=100:1). 4M Hydrogen chloride/ethyl acetate (0.25 ml) was added to the combined solution which contained the target compound, and the reaction solution was concentrated. The obtained solids were washed with hot methanol to give Compound 64 (87 mg).

Example 29

Aqueous 30% hydrogen peroxide (20 ml) was added to a solution of a free form of Compound 127 (900 mg) in acetic acid (20 ml) and the mixture was stirred at 70° C. for 11 hours. After being left to cool, the reaction mixture was diluted with chloroform, washed with water, 5% aqueous sodium thiosulfate and saturated aqueous sodium hydrogencarbonate, and dried over anhydrous magnesium sulfate. Silica gel (9 ml) was added to the organic layer. It was concentrated and subjected to silica gel column chromatography (eluent:chloroform:methanol=100:1). 4M Hydrogen chloride/ethyl acetate (1.0 ml) was added to the collected solution which contained the target compound, and the solution was concentrated. The obtained solids were washed with methanol-ether to give Compound 65 (350 mg).

Example 30

Potassium carbonate (450 mg) and 2-methoxy-5-nitrobenzyl bromide (480 mg) were added to a solution of Compound y2 (400 mg) in DMF (10 ml) and the mixture was stirred at room temperature for 5.5 hours. The reaction solution was diluted with chloroform, washed with water and dried over anhydrous magnesium sulfate. The obtained organic layer was concentrated and crystallized from diethyl ether-hexane to give Compound 66 (558 mg).

Example 31

Methylhydrazine (460 mg) was added to a solution of Compound r1 (1.8 g) in methanol (30 ml) and the mixture was stirred for 6 hours. The reaction solution was concentrated under reduced pressure, and the obtained residue was washed with water and dissolved in pyridine (5.0 ml). 2-Methyl-5-nitrobenzenesulfonyl chloride (700 mg) was added to it and the reaction solution was stirred for 18 hours, followed by purification with silica gel column chromatography (eluent:chloroform:methanol=20:1). 4M Hydrogen chloride/ethyl acetate (3.0 ml) was added to the collected solution which contained the target compound, and a precipitated solid was collected to give Compound 67 (150 mg).

Example 32

Compound p2 (250 mg) was added to trifluoroacetic acid (1.5 ml) and the mixture was stirred for 2 hours, followed by concentration under reduced pressure and azeotrope with ethanol. THF (3.0 ml) and 60% sodium hydride (80 mg) were added to this and the reaction mixture was stirred for 15 minutes. Then, 2-methyl-5-nitrobenzenesulfonyl chloride (240 mg) was added and the reaction solution was stirred for 4 hours, concentrated under reduced pressure, washed with water, and dissolved in methanol (2.0 ml). 4M Hydrogen chloride/ethyl acetate (1.0 ml) was added and the solution was concentrated under reduced pressure. The residue was washed with methanol to give Compound 68 (140 mg).

Example 33

Potassium hydroxide (1.6 g) was added to a solution of Compound t1 (800 mg) in water-methanol (5.0–5.0 ml) and the mixture was stirred at 90° C. for 3 hours. 1M hydrochloric acid was added to neutralize the reaction solution. Then, the reaction solution was concentrated under reduced pressure. Ethanol was added to the obtained residue, followed by filtration and concentration of filtrate under reduced pressure, wherein this sequence of operations were repeated 3 times. The obtained residue was dissolved in ethanol amine (5.0 ml), stirred at 200° C. for 1 hour and then poured into water. The resulting precipitates were collected. To a THF (5.0 ml) solution of this material, 60% sodiumn hydride (60 mg) and 2-methyl-5-nitrobenzenesulfonyl chloride (350 mg) were added. The reaction mixture was stirred for 4 hours and purified with silica gel column chromatography (eluent:chloroform:methanol=20:1). 4M Hydrogen chloride/ethyl acetate (1.0 ml) was added to the collected solution which contained the target compound, and the reaction solution was concentrated under reduced pressure. The obtained residue was washed with ethanol to give Compound 69 (170 mg).

Example 34

Acetic acid (15 ml) was added to Compound n4 (1.45 g) and the mixture was stirred at 75° C. overnight. After being allowed to cool, the reaction solution was concentrated and crystallized from ethanol to give Compound 70 (1.17 g).

What is claimed is:

1. An imidazolidine derivative represented by formula (I) or salts thereof;

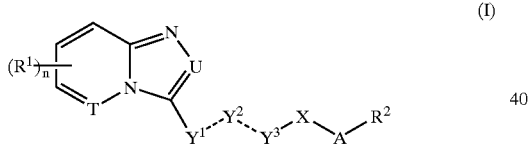

wherein $R^1$ represents —H, -a lower alkyl, -a lower alkenyl, lower alkyl, -a cycloatkyl, -a cycloalkenyl, -a halogen, —$NO_2$, —CN, -a halogenated lower alkyl, —$OR^a$, —$SR^a$, —$SO_2R^a$, —$SOR^a$, —$CO_2R^a$, —CO—$R^a$, -an aryl, -a lower alkylene-an aryl, —O-a lower alkylene-an aryl, —$CONR^aR^b$, —CO-(a nitrogen-containing saturated heterocyclic group which may be substituted by a lower alkyl group), —$SO_2NR^aR^b$, —$SO_2$-(a nitrogen-containing saturated heterocyclic group which may be substituted by a lower alkyl group), —$SO_3H$, -(a nitrogen-containing saturated heterocyclic group which may be substituted by a lower alkyl group), —$NR^aR^b$, —$CONR^a$-a lower alcylene-$OR^b$, —$CONR^a$-a lower alkylene-$NR^bR^c$, —$CONR^a$-a lower alkylene-(a nitrogen-containing saturated heterocyclic group which may be substituted by a lower alkyl group), —O-a lower alkylene-$OR^a$, —O-a lower alkylene-O-a lower alkylene-$OR^a$, —O-a lower alkylene-$NR^aR^b$, —O-a lower alkylene-(a nitrogen-containing saturated heterocyclic group which may be substituted by a lower alkyl group), —O-a lower alkylene-O-a lower alkylene-$NR^aR^b$, —O-a lower alkylene-O-a lower alkylene-(a nitrogen-containing saturated hetermcyclic group which may be substituted by a lower alkyl group), —O-a lower alkylene-$NR^c$-a lower alkylene-$NR^aR^b$, —O-a lower alkylene-$NR^c$-a lower alkylene-(a nitrogen-containing saturated heterocyclic group which may be substituted by a lower alkyl group), —$OCO$—$NR^aR^b$, —$OCO$-(a nitrogen-containing saturated heterocyclic group which may be substituted by a lower alkyl group), —$NR^a$-$SO_2R^b$, —$NR^c$-a lower alkylene-$NR^aR^b$, —$NR^c$-a lower alkylene-(a nitrogen-containing saturated heterocyclic group which may be substituted by a lower alkyl group), —N(a lower alkylene-$NR^aR^b$)$_2$, —N(a lower alkylene-(a nitrogen-containing saturated heterocyclic group which may be substituted by a lower alkyl group))$_2$, —$CONR^a$—$OR^b$, —$NR^a$—$COR^b$, —$NR^a$—CO—$NR^bR^c$, —$NR^a$—CO-(a nitrogen-containing saturated heterocyclic group which may be substituted by a lower alkyl group), or —$OCOR^a$;

$R^a$, $R^b$ and $R^c$ which may be the same or different, represent —H, -a lower alkyl or -an aryl;

T represents N or $CR^{1a}$,

U represents N or $CR^3$;

N represents an integer, 1, 2 or 3;

in $Y^1 \ldots Y^2 \ldots Y^3$,

... represents a single bond on one side and a single or double bond on the other side, $Y^1$ represents $CR^5$ or $CR^{5a}R^{5b}$, $Y^2$ represents N, NH, $CR^{4a}$ or $CR^{4b}R^{4c}$, and $Y^3$ represents $NR^6$, $CR^{4d}$ or $CR^{4e}R^{4f}$, whereas $Y^3$ represents $NR^6$ when $Y^2$ represents $CR^{4a}$ or $CR^{4b}R^{4c}$;

X represents S, SO or $SO_2$;

"A" represents a linkage, a lower alkylene, a lower alkenylene or a lower alkenylene;

$R^2$ represents -a lower alkyl which may have one or more substituents, -a lower alkenyl which may have one or more subsituents, -a lower alkynyl which may have one or more subsituents, -a cycloalkyl which may have one or more subsituents, -a cycloalkenyl which may have one or more subsituents, —N=O, -an aryl which may have one or more subsituents, or -a heteroaryl which may have one or more subsituents;

$R^{1a}$, $R^3$, $R^{4a}$, $R^{4b}$, $R^{4c}$, $R^{4d}$, $R^{4e}$, $R^{4f}$, $R^{5a}$, and $R^{5b}$, which may be the same or different, represent a group defined by $R^1$, whereas $R^{4b}$ and $R^{4c}$, $R^{4c}$ and $R^{4f}$, or $R^{5a}$ and $R^{5b}$ may be combined with each other to form an oxo group (=O);

$R^5$ and $R^6$ which may be the same or different, represent —H, -a lower alkyl which may have one or more subsituents, -a lower alkenyl which may have one or more subsituents, -a lower alkynyl which may have one or more subsituents.

2. The imidazopyiridine derivative or a salt thereof according to claim 1, wherein $R^1$ represents —H, -a lower alkyl, -a lower alkenyl -a lower alkynyl, -a cycloalkyl, -a cycloalkenyl, -a halogen, —$NO_2$, —CN, -a halogenated lower alkyl, —OH, —O-a lower alkyl, —O-an aryl, —SH, —S-a lower alkyl, —$SO_2$-a lower alkyl, —SO-a lower alkyl, —COOH, —COO-a lower alkyl, —CO-a lower alkyl, -an aryl —CO-an aryl, -a lower alkylene-an aryl, —O-a lower alkylene-an aryl, —$CONH_2$, —$SO_2NH_2$, —$SO_3H$, -a nitrogen-containing saturated heterocyclic group, —$NH_2$, —NH-a lower alkyl or —N(a lower alkyl)$_2$; T represents $CR^{1a}$; U represents $CR^3$; in $Y^1 \ldots Y^2 \ldots Y^3, \ldots$ represents a single bond on one side and a single or double bond on the other side, $Y^1$ represents $CR^5$ or $CHR^{5a}$, $Y^2$ represents N, $CR^{4a}$ or $CHR^{4b}$, and $Y^3$ represents $NR^7$, $CR^{4d}$ or $CHR^{4e}$; $R^2$ represents -a halogenated loweralkyl, —N=O, -an aryl which may have one or more subsituents, or -a heteroaryl which may have one or more subsituents; $R^{1a}$, $R^3$, $R^{4a}$, $R^{4b}$, $R^{4d}$ and $R^{4e}$, which may be the same or different, represent a group defined by $R^1$; and $R^5$, $R^{5a}$ and $R^6$, which may be the same or different, represents —H, or -a lower alkyl.

3. The imidazopyridine derivative or a salt thereof according to claim 1, wherein n represents 1; and $R^1$ represents -a lower alkyl, a halogen, —CN, —NO$_2$, -a halogenated lower alkyl, —OR$^a$, —O-a lower alkylene-an aryl, —COOR$^a$, —CONR-a lower alkylene-OR$^b$, —CONR$^a$R$^b$, —CO-(a nitrogen-containing saturated heterocyclic group which may be substituted by a lower alkyl group), —CONR$^a$-a lower alkylene—NR$^b$R$^c$, —CONR$^a$-a lower alkylene-(a nitrogen-containing saturated heterocyclic group which may be substituted by a lower alkyl group), or -an aryl.

4. The imidazopyridine derivative or a salt thereof according to claim 1, wherein A represents a linkage and $R^2$ represents -an aryl which may have one or more substituents or -a heteroaryl which may have one or more substituents.

5. The imidazopyridine derivative or a salt thereof according to claim 4, wherein $R^2$ represents a phenyl which may have one or more substituents selected from the group consisting of -(a lower alkyl which may be substituted by —OH), -a lower alkenyl, -a halogen, —NO$_2$, —CN, -a halogenated lower alkyl, —O-a halogenated lower alkyl, —OH, —O-a lower alkyl, —CO-a lower alkyl, —SO$_2$-a lower alkyl, —COOH, —COO-a lower alkyl, —CONH$_2$, —SO$_2$NH$_2$, —CO-an aryl, —SO$_2$-an aryl, —NH$_2$, —NH-a lower alkyl, —N(a lower alkyl)$_2$, -(a nitrogen-containing saturated heterocyclic group which may be substituted by a lower alkyl group), —NHCO-a lower alkyl, -an aryl which may be substituted by 1 to 5 substituents selected from Group E, and -a heteroaryl which may be substituted by 1 to 5 substituents selected from Group E, whereas Group E consists of -a lower alkyl, -a lower alkenyl, -a lower alkynyl, -a halogen, —NO$_2$, —CN, —OH, —O-a lower alkyl, —O-a halogenated lower alkyl, —SH, —S-a lower alkyl, —SO$_2$-a lower alkyl, —SO-a lower alkyl, —COOH, —COO-a lower alkyl, —CO-a lower alkyl, —CONH$_2$, —NH$_2$, —NH-a lower alkyl, —N(a lower alkyl)$_2$, -(a nitrogen-containing saturated heterocyclic group which may be substituted by a lower alkyl group), -an aryl, -a heteroaryl, -a cycloalkyl and -a cycloalkenyl.

6. The imidazopyridine derivative or a salt thereof according to claim 1, wherein X represents SO$_2$.

7. The imidazopyridine derivative or a salt thereof according to claim 1, wherein $Y^1 \ldots Y^2 \ldots Y^3$ represents CR$^5$=N—NR$^6$, CR$^{5a}$R$^{5b}$—NH—NR$^6$ or CR$^{5a}$R$^{5b}$—CR$^{4b}$R$^{4c}$—NR$^6$.

8. The imidazopyridine derivative or a salt thereof according to claim 7, wherein $Y^1 \ldots Y^2 \ldots Y^3$ represents CR$^5$=N—NR$^6$; R$^5$ represents —H or a lower alkyl; and R$^6$ represents —H, -a lower alkyl or -a lower alkenyl, wherein -a lower alkyl or -a lower alkenyl may be substituted by one or more substituents selected from a group consisting of —O-a lower alkyl, —S-a lower alkyl, —SO$_2$-a lower alkyl, —SO-a lower alkyl, —COOH, —COO-a lower alkyl, —CO-a lower alkyl, —CONH$_2$, —NH$_2$, —NH-a lower alkyl, —N(a lower alkyl)$_2$, -(a nitrogen-containing saturated heterocyclic group which may be substituted by a lower alkyl group) and -an aryl.

9. The imidazopyridine derivative or a salt thereof according to claim 1, which is selected from the group consisting of 2'-[(6-bromoimidazo[1,2-a]pyridin-3-yl)methylidene]-1', 2-dimethyl-5-nitrobenzenesulfonohydrazide; 2'-[(6-bromoimidazo[1,2-a]pyridin-3-yl)methylidene]-2-ethyl-1'-methyl-5-nitrobenzenesulfonohydrazide; 3-({2-[(6-bromoimidazo[1,2-a]pyridin-3-yl)methylidene]-1-methylhydrazino}sulfonyl)-4-methylbenzonitrile; 2'-[(6-fluoroimidazo[1,2-a]pyridin-3-yl)methylidene]-1',2-dimethyl-5-nitrobenzenesulfonohydrazide; 2-amino-2'-[(6-chloroimidazo[1,2-a]pyridin-3-yl)methylidene]-1'-methyl-5-nitrobenzenesulfonohydrazide; 2'-[(6-chloroimidazo[1,2-a]pyridin-3-yl)methylidene]-1'-methyl-5-nitro-2-(2,2,2-trifluoroethoxy)benzenesulfonohydrazide; 6-bromo-3-{[(2-methyl-5-nitrobenzenesulfonyl)(2-morpholinoethyl)hydrazono]methyl}imidazo[1,2-a]pyridine; 6chloro-3-{[(methyl)(2-methyl-5-nitrobenzenesulfonyl)hydrazono]methyl}imidazo[1,2-a]pyridine; 3-{[(methyl)(2-methyl-5-nitrobenzenesulfonyl)hydrazono]methyl}imidazo[1,2-a]pyridine-6carbonitrile; 5-cyano-2'-[(6-fluoroimidazo[1,2-a]pyridin-3-yl)methylidene]-1',2-dimethylbenzenesulfonohydrazide; 5-cyano-2'-[(6-cyanoimidazo[1,2-a]pyridin-3-yl)methylidene]-1',2-dimethylbenzenesulfonohydrazide; 1'2-dimethyl-2'-[(6-methylimidazo[1,2-a]pyridin-3-yl)methylidene]-5-nitrobenzenesulfonohydrazide; 2'-[(6chloroimidazo[1,2-a]pyridin-3-yl)methylidene]-2-(1H-imidazol-1-yl)-1'-methyl-5-nitrobenzenesulfonohydrazide; 2'-[(6-chloroimidazo[1,2-a]pyridin-3-yl)methylidene]-2-dimethylamino-1'-methyl-5-nitrobenzenesulfonohydrazide; and salts thereof.

10. A method to treat disorders in which phosphatidylinositol 3-kinase plays a role, wherein the method comprises of administering to a patient an effective amount of the imidazopyridine derivative or a salt thereof according to claim 1.

11. The method of claim 10 to treat disorders in which phosphatidylinositol 3-kinase plays a role, wherein the disorders in which phosphatidylinositol 3-kinase plays a role are cancers.

12. A pharmaceutical composition comprising the imidazopyridine derivative or a salt thereof according to claim 1 and a pharmaceutically acceptable carrier.

* * * * *

UNITED STATES PATENT AND TRADEMARK OFFICE
CERTIFICATE OF CORRECTION

PATENT NO. : 6,403,588 B1
DATED : June 11, 2002
INVENTOR(S) : Hayakawa et al.

It is certified that error appears in the above-identified patent and that said Letters Patent is hereby corrected as shown below:

Column 3,
Line 27, delete "$O^a$" and substitute -- $OR^a$ --.

Column 4,
Line 10, delete "alkenylene" and substitute -- alkynylene --;
Line 19, after "$R^{4a}$", insert -- $R^{4b}$ --;

Column 5,
Line 12, delete "alkenylene" and substitute -- alkynylene --;

Column 6,
Line 66, delete "$R^{4c}$" and substitute -- $R^{4e}$ --;

Column 8,
Lines 11 and 12, delete "$N^6$" and substitute -- $NR^6$ --;

Column 10,
Line 27, delete "B 1" and substitute -- B1 --;

Column 32,
(Table 3), at line q1, column 3, replace "757" with -- 7.57 --;

Column 45,
(Table 8), for compound 51, in the structure, replace "Mw" with -- Me --;

Column 48,
(Table 9), structure for compound 78, replace "Me" with -- OMe --;
(Table 9), structure for compounds 79 and 80, delete "Me" and substitute -- OMe --;
(Table 9), structure for compound 87, delete "Me" and substitute -- Ome --;

Column 63,
Table 19, line 35, delete the structure

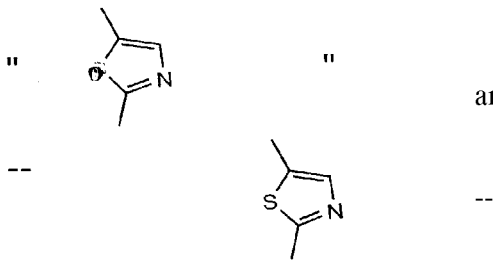

and replace the structure with the following:

UNITED STATES PATENT AND TRADEMARK OFFICE
CERTIFICATE OF CORRECTION

PATENT NO. : 6,403,588 B1
DATED : June 11, 2002
INVENTOR(S) : Hayakawa et al.

It is certified that error appears in the above-identified patent and that said Letters Patent is hereby corrected as shown below:

<u>Column 65,</u>
Table 19, line 30, delete the structure

" 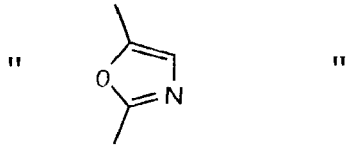 " and replace the structure with the following

-- 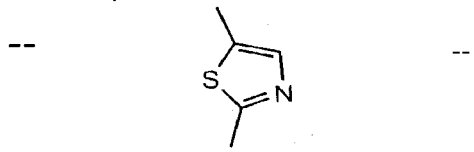 --

<u>Column 78,</u>
Line 22, delete "N" and substitute -- n --;
Line 33, delete "alkenylene" and substitute -- alkynylene --.

<u>Column 80,</u>
Line 25, replace "6chloro" with -- 6-chloro --;
Line 29, replace "6carbonitrile" with -- 6-carbonitrite --;

Signed and Sealed this

Twenty-sixth Day of August, 2003

JAMES E. ROGAN
*Director of the United States Patent and Trademark Office*